U S 0 1 2 1 1 4 9 7 5 B 2

US012114975B2

(12) United States Patent
Bohm et al.

(10) Patent No.: US 12,114,975 B2
(45) Date of Patent: Oct. 15, 2024

(54) ANALYTE SENSOR WITH IMPEDANCE DETERMINATION

(71) Applicant: DexCom, Inc., San Diego, CA (US)

(72) Inventors: Sebastian Bohm, San Diego, CA (US); Anna Claire Harley-Trochimczyk, San Diego, CA (US); Daiting Rong, San Diego, CA (US); Rui Ma, San Diego, CA (US); Wenjie Lan, San Diego, CA (US); Minglian Shi, San Diego, CA (US); Disha B. Sheth, Oceanside, CA (US)

(73) Assignee: Dexcom, Inc., San Diego, CA (US)

( * ) Notice: Subject to any disclaimer, the term of this patent is extended or adjusted under 35 U.S.C. 154(b) by 1033 days.

(21) Appl. No.: 16/728,652

(22) Filed: Dec. 27, 2019

(65) Prior Publication Data

US 2020/0205694 A1 Jul. 2, 2020

Related U.S. Application Data

(60) Provisional application No. 62/786,208, filed on Dec. 28, 2018, provisional application No. 62/786,166, (Continued)

(51) Int. Cl.
*A61B 5/1495* (2006.01)
*A61B 5/00* (2006.01)
(Continued)

(52) U.S. Cl.
CPC .......... *A61B 5/1495* (2013.01); *A61B 5/0537* (2013.01); *A61B 5/14532* (2013.01); (Continued)

(58) Field of Classification Search
CPC .............. A61B 5/0537; A61B 5/14532; A61B 5/14546; A61B 5/1473; A61B 5/1486; (Continued)

(56) References Cited

U.S. PATENT DOCUMENTS

| 5,800,420 A | 9/1998 | Gross et al. |
| 6,001,067 A | 12/1999 | Shults et al. |
| (Continued) | | |

FOREIGN PATENT DOCUMENTS

| GB | 1505343 A | 3/1978 |
| JP | 2000171431 A | 6/2000 |
| (Continued) | | |

OTHER PUBLICATIONS

International Search Report and Written Opinion for Application No. PCT/US2019/068713 mailed on Apr. 16, 2020, 11 pages.

*Primary Examiner* — Alexander Satanovsky
*Assistant Examiner* — Sharah Zaab
(74) *Attorney, Agent, or Firm* — Schwegman, Lundberg & Woessner, P.A.

(57) ABSTRACT

Various examples are directed to systems and methods for operating an analyte sensor system using sensor electronics. An example method may comprise applying a bias voltage change to an analyte sensor bias voltage and measuring a current value for each of a plurality of time periods after application of the bias voltage change. The example method may also comprise determining an estimated impedance using the current values for the plurality of time periods and determining a characteristic of the analyte sensor using the estimated impedance. The example method may further comprise receiving from the analyte sensor a signal indicative of an analyte concentration, and determining an estimated analyte concentration level using the determined characteristic of the analyte sensor and the received signal.

32 Claims, 21 Drawing Sheets

Related U.S. Application Data filed on Dec. 28, 2018, provisional application No. 62/786,127, filed on Dec. 28, 2018, provisional application No. 62/786,228, filed on Dec. 28, 2018, provisional application No. 62/786,116, filed on Dec. 28, 2018.

(51) Int. Cl.
| | |
|---|---|
| *A61B 5/0537* | (2021.01) |
| *A61B 5/145* | (2006.01) |
| *A61B 5/1473* | (2006.01) |
| *A61B 5/1486* | (2006.01) |
| *G01N 27/02* | (2006.01) |
| *G01N 27/22* | (2006.01) |
| *G01N 27/24* | (2006.01) |
| *G01N 33/487* | (2006.01) |

(52) U.S. Cl.
CPC ........ *A61B 5/14546* (2013.01); *A61B 5/1473* (2013.01); *A61B 5/1486* (2013.01); *A61B 5/14865* (2013.01); *A61B 5/6844* (2013.01); *G01N 27/221* (2013.01); *G01N 27/24* (2013.01); *G01N 33/48707* (2013.01); *A61B 5/0004* (2013.01); *A61B 5/0031* (2013.01); *A61B 2560/0223* (2013.01); *A61B 2560/0252* (2013.01); *A61B 2560/0276* (2013.01); *G01N 27/026* (2013.01)

(58) Field of Classification Search
CPC . A61B 5/14865; A61B 5/6844; A61B 5/0004; A61B 5/0031; A61B 2560/0223; A61B 2560/0252; A61B 2560/0276; G01N 27/221; G01N 27/24; G01N 33/48707; G01N 27/026
See application file for complete search history.

(56) References Cited

U.S. PATENT DOCUMENTS

| | | | |
|---|---|---|---|
| 6,424,847 B1 | 7/2002 | Mastrototaro et al. | |
| 6,477,395 B2 | 11/2002 | Schulman et al. | |
| 6,484,046 B1 | 11/2002 | Say et al. | |
| 6,512,939 B1 | 1/2003 | Colvin et al. | |
| 6,565,509 B1 | 5/2003 | Say et al. | |
| 6,579,690 B1 | 6/2003 | Bonnecaze et al. | |
| 7,494,465 B2 | 2/2009 | Brister et al. | |
| 8,372,266 B2 | 2/2013 | Biswas et al. | |
| 8,682,408 B2 | 3/2014 | Boock et al. | |
| 8,834,707 B2 | 9/2014 | Milam et al. | |
| 9,044,199 B2 | 6/2015 | Brister et al. | |
| 9,481,917 B2 | 11/2016 | Bochiechio et al. | |
| 9,808,190 B2 | 11/2017 | Bohm et al. | |
| 2002/0098119 A1* | 7/2002 | Goodman | G01N 27/128 436/151 |
| 2003/0191376 A1* | 10/2003 | Samuels | A61B 5/150099 600/309 |
| 2005/0027463 A1 | 2/2005 | Goode, Jr. et al. | |
| 2005/0043598 A1* | 2/2005 | Goode | A61B 5/1473 600/347 |
| 2006/0020187 A1 | 1/2006 | Brister et al. | |
| 2007/0027385 A1 | 2/2007 | Brister et al. | |
| 2007/0128681 A1 | 6/2007 | Barman et al. | |
| 2007/0197890 A1 | 8/2007 | Boock et al. | |
| 2007/0299617 A1 | 12/2007 | Willis | |
| 2008/0108942 A1 | 5/2008 | Brister et al. | |
| 2008/0119703 A1 | 5/2008 | Brister et al. | |
| 2008/0156661 A1 | 7/2008 | Cooper et al. | |
| 2010/0196203 A1* | 8/2010 | Sanghera | G01N 33/48728 422/68.1 |
| 2011/0024307 A1 | 2/2011 | Simpson et al. | |
| 2012/0003687 A1 | 1/2012 | Toner et al. | |
| 2012/0004524 A1 | 1/2012 | Van Antwerp et al. | |
| 2012/0262298 A1* | 10/2012 | Bohm | A61B 5/7267 73/61.76 |
| 2012/0265037 A1* | 10/2012 | Bohm | G01N 33/49 600/309 |
| 2013/0245981 A1* | 9/2013 | Estes | A61B 5/7203 702/87 |
| 2014/0005509 A1 | 1/2014 | Bhavaraju et al. | |
| 2015/0351672 A1* | 12/2015 | Vanslyke | A61B 5/7246 600/301 |
| 2017/0181672 A1* | 6/2017 | Nogueira | A61B 5/6848 |
| 2017/0184527 A1 | 6/2017 | Nogueira et al. | |
| 2017/0228345 A1 | 8/2017 | Gupta et al. | |
| 2017/0281092 A1 | 10/2017 | Burnette et al. | |
| 2017/0311852 A1 | 11/2017 | Morgan | |
| 2018/0279928 A1 | 10/2018 | Previl | |
| 2018/0325430 A1 | 11/2018 | Vaddiraju et al. | |
| 2018/0372667 A1 | 12/2018 | Gupta | |
| 2019/0004005 A1 | 1/2019 | Oja et al. | |
| 2019/0227022 A1 | 7/2019 | Harley-Trochimczyk et al. | |

FOREIGN PATENT DOCUMENTS

| | | |
|---|---|---|
| JP | 2015509803 A | 4/2015 |
| WO | 2012154548 A1 | 11/2012 |
| WO | 2019007842 A1 | 1/2019 |

* cited by examiner

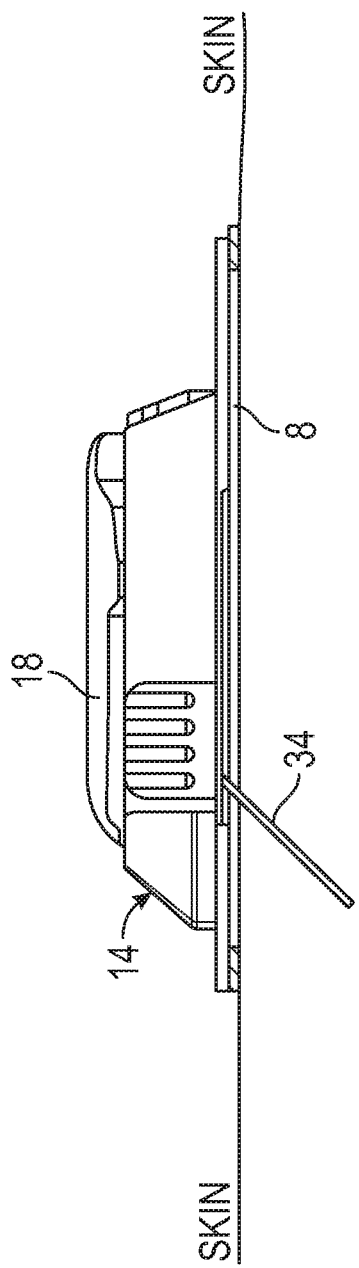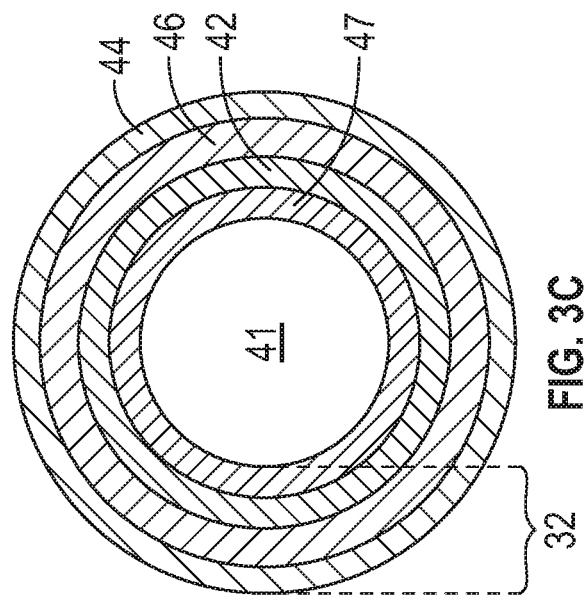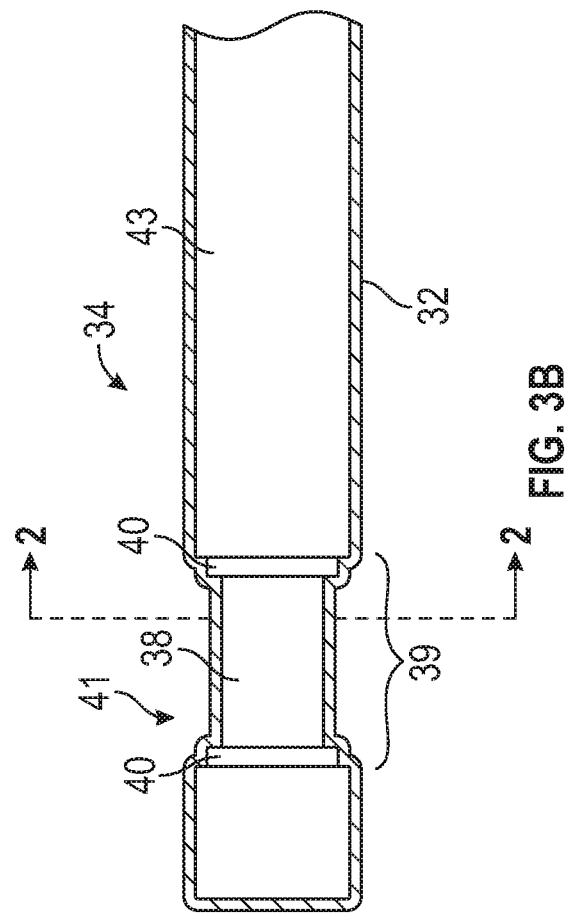

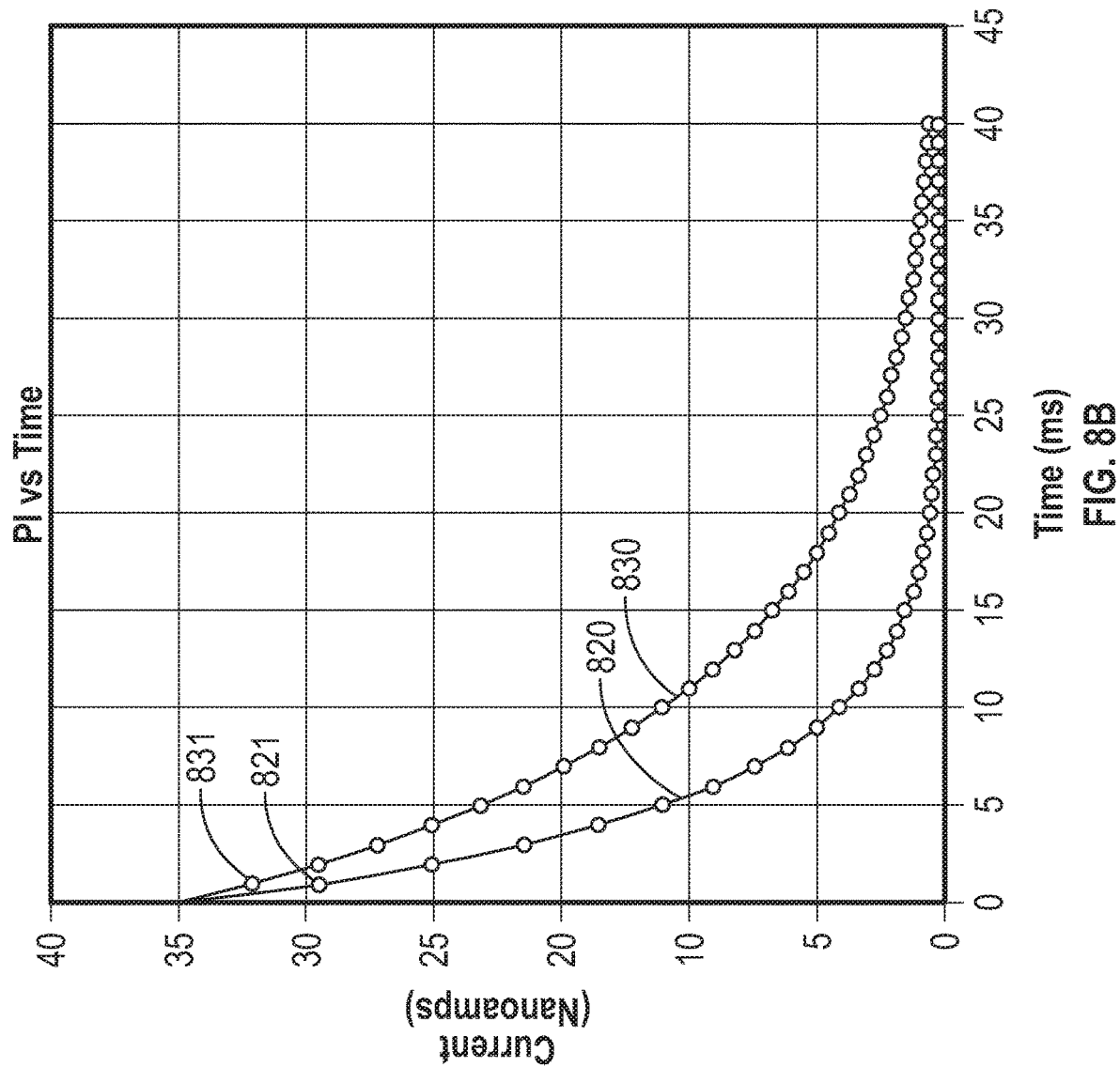

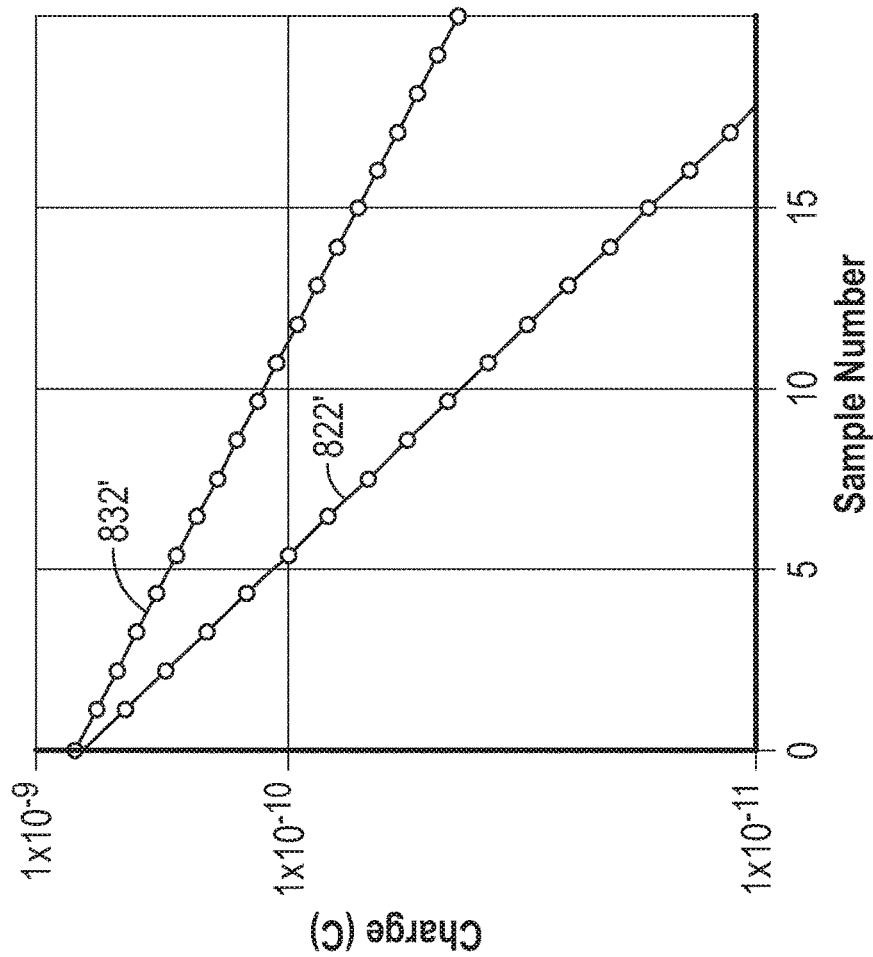
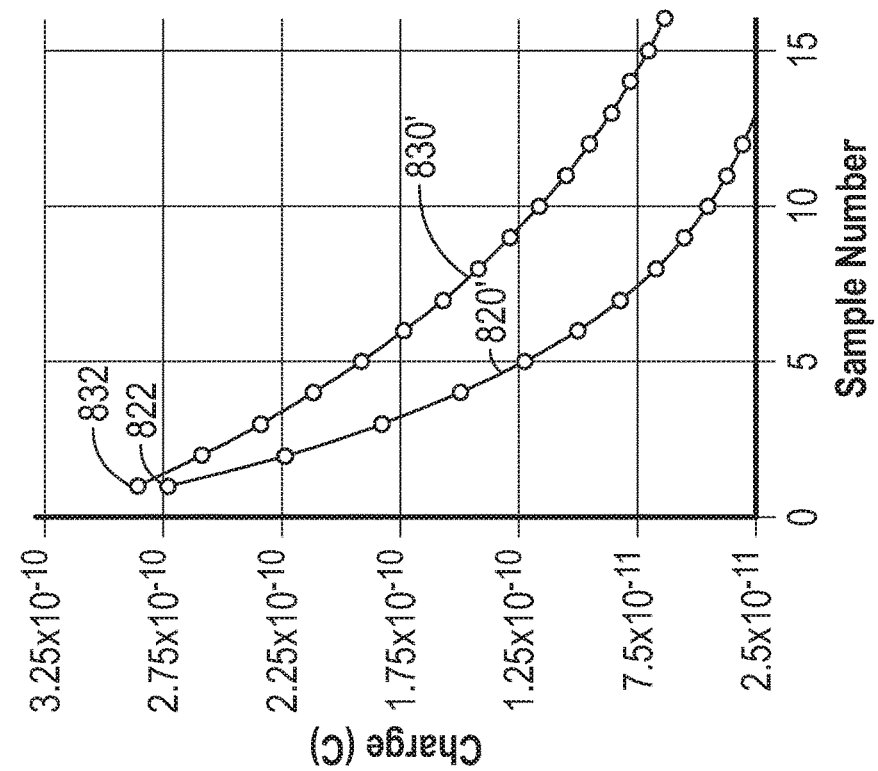
FIG. 8C
FIG. 8D

ANALYTE SENSOR WITH IMPEDANCE DETERMINATION

INCORPORATION BY REFERENCE TO RELATED APPLICATIONS

Any and all priority claims identified in the Application Data Sheet, or any correction thereto, are hereby incorporated by reference under 37 CFR 1.57. This application claims the benefit of U.S. Provisional Application Ser. No. 62/786,166, filed on Dec. 28, 2018, U.S. Provisional Application Ser. No. 62/786,116, filed on Dec. 28, 2018, U.S. Provisional Application Ser. No. 62/786,208, filed on Dec. 28, 2018, U.S. Provisional Application Ser. No. 62/786,127, filed on Dec. 28, 2018, and U.S. Provisional Application Ser. No. 62/786,228, filed on Dec. 28, 2018. Each of the aforementioned applications is incorporated by reference herein in its entirety, and each is hereby expressly made a part of this specification.

TECHNICAL FIELD

The present development relates generally to medical devices such as analyte sensors, and more particularly, but not by way of limitation, to systems, devices, and methods that use impedance measurements in a continuous glucose monitoring system.

BACKGROUND

Diabetes is a metabolic condition relating to the production or use of insulin by the body. Insulin is a hormone that allows the body to use glucose for energy, or store glucose as fat.

When a person eats a meal that contains carbohydrates, the food is processed by the digestive system, which produces glucose in the person's blood. Blood glucose can be used for energy or stored as fat. The body normally maintains blood glucose levels in a range that provides sufficient energy to support bodily functions and avoids problems that can arise when glucose levels are too high, or too low. Regulation of blood glucose levels depends on the production and use of insulin, which regulates the movement of blood glucose into cells.

When the body does not produce enough insulin, or when the body is unable to effectively use insulin that is present, blood sugar levels can elevate beyond normal ranges. The state of having a higher than normal blood sugar level is called "hyperglycemia." Chronic hyperglycemia can lead to a number of health problems, such as cardiovascular disease, cataract and other eye problems, nerve damage (neuropathy), and kidney damage. Hyperglycemia can also lead to acute problems, such as diabetic ketoacidosis—a state in which the body becomes excessively acidic due to the presence of blood glucose and ketones, which are produced when the body cannot use glucose. The state of having lower than normal blood glucose levels is called "hypoglycemia." Severe hypoglycemia can lead to acute crises that can result in seizures or death.

A diabetes patient can receive insulin to manage blood glucose levels. Insulin can be received, for example, through a manual injection with a needle. Wearable insulin pumps are also available. Diet and exercise also affect blood glucose levels. A glucose sensor can provide an estimated glucose concentration level, which can be used as guidance by a patient or caregiver.

Diabetes conditions are sometimes referred to as "Type 1" and "Type 2." A Type 1 diabetes patient is typically able to use insulin when it is present, but the body is unable to produce sufficient amounts of insulin, because of a problem with the insulin-producing beta cells of the pancreas. A Type 2 diabetes patient may produce some insulin, but the patient has become "insulin resistant" due to a reduced sensitivity to insulin. The result is that even though insulin is present in the body, the insulin is not sufficiently used by the patient's body to effectively regulate blood sugar levels.

Blood sugar concentration levels may be monitored with an analyte sensor, such as a continuous glucose monitor. A continuous glucose monitor may provide the wearer (patient) with information, such as an estimated blood glucose level or a trend of estimated blood glucose levels.

This Background is provided to introduce a brief context for the Summary and Detailed Description that follow. This Background is not intended to be an aid in determining the scope of the claimed subject matter nor be viewed as limiting the claimed subject matter to implementations that solve any or all of the disadvantages or problems presented above.

SUMMARY

This present application discloses, among other things, systems, devices, and methods for use of impedance or conductance measurements or estimates in an analyte sensor, such as a glucose sensor.

Example 1 is a method of operating an analyte sensor system using sensor electronics. The method comprises applying a bias voltage change to an analyte sensor bias voltage and measuring a current values for each of a plurality of time periods after application of the bias voltage change. The method also comprises determining an estimated impedance using the current values for the plurality of time periods and determining a characteristic of the analyte sensor using the estimated impedance. The method further comprises receiving from the analyte sensor a signal indicative of an analyte concentration and determining an estimated analyte concentration level using the determined characteristic of the analyte sensor and the received signal.

In Example 2, the subject matter of Example 1 optionally includes wherein measuring the current includes integrating a charge over each of the specified time periods.

In Example 3, the subject matter of any one or more of Examples 1-2 optionally includes wherein determining an impedance includes fitting a curve using the determined currents for the plurality of time periods, and determining the impedance based on the fitted curve.

In Example 4, the subject matter of Example 3 optionally includes wherein fitting the curve includes fitting an exponential curve, wherein the exponential curve accounts for the impact of double-layer capacitance on the measured current response.

In Example 5, the subject matter of any one or more of Examples 1-4 optionally includes wherein determining a characteristic of the analyte sensor includes determining a sensitivity of the analyte sensor to an analyte concentration.

In Example 6, the subject matter of Example 5 optionally includes compensating for sensor drift using the determined impedance or the determined sensitivity.

In Example 7, the subject matter of any one or more of Examples 1-6 optionally includes wherein determining a characteristic of the analyte sensor includes determining a level of damage or defect of the sensor.

In Example 8, the subject matter of any one or more of Examples 1-7 optionally includes wherein determining a characteristic of the analyte sensor includes determining a compensation for the sensor.

In Example 9, the subject matter of any one or more of Examples 1-8 optionally includes wherein applying a change to an analyte sensor bias voltage includes applying a step in the bias voltage.

Example 10 is an analyte sensor system comprising an analyte configured to provide a sensor signal indicative of an analyte concentration level and sensor electronics coupled to the analyte sensor. The sensor electronics are to apply a change to an analyte sensor bias voltage, measure a plurality of current response levels for each of a plurality of respective time periods after application of the change to the bias voltage, determine an estimated impedance using the plurality of current response levels, receive a signal indicative of an analyte concentration from the analyte sensor, and determine an estimated analyte concentration level based upon the received signal and the estimated impedance.

In Example 11, the subject matter of Example 10 optionally includes wherein measuring a plurality of current response levels includes integrating charge over each of the plurality of respective time periods.

In Example 12, the subject matter of any one or more of Examples 10-11 optionally includes wherein determining an estimated impedance includes fitting a curve using the measured current response levels and determining the estimated impedance using the fitted curve.

In Example 13, the subject matter of Example 12 optionally includes wherein fitting the curve includes fitting an exponential curve, wherein the exponential curve account for the impact of double-layer capacitance on the measured current response.

In Example 14, the subject matter of any one or more of Examples 10-13 optionally includes wherein the sensor electronics are configured to determine a sensor sensitivity to the analyte using the estimated impedance and determine the estimated analyte concentration level using the sensor sensitivity.

In Example 15, the subject matter of Example 14 optionally includes wherein determining a sensor sensitivity includes determining a sensor compensation based on the estimated impedance.

In Example 16, the subject matter of any one or more of Examples 10-15 optionally includes wherein determining an estimated impedance using the plurality of current response levels accounts for a double-layer membrane capacitance of the sensor.

Example 17 is a method of operating an analyte sensor system using sensor electronics to correct for an error from double-layer capacitance of a sensor membrane. The method comprises applying a change to an analyte sensor bias voltage and measuring a current value for each of a plurality of time periods after application of the bias voltage change. The method also comprises determining a current at the time of the bias voltage change using the current values for the plurality of time periods and determining an estimated impedance using the determined current at the time of the bias voltage change. The method further comprises determining a characteristic of the analyte sensor using the estimated impedance, receiving from the analyte sensor a signal indicative of an analyte concentration, and determining an estimated analyte concentration level using the determined characteristic of the analyte sensor and the received signal.

In Example 18, the subject matter of Example 17 optionally includes fitting the current values for the plurality of time periods to an exponential curve, and extrapolating the fitted curve to determine the current at the time of the bias voltage change.

In Example 19, the subject matter of any one or more of Examples 17-18 optionally includes wherein determining the characteristic of the analyte sensor includes determining a sensor sensitivity.

In Example 20, the subject matter of Example 19 optionally includes updating sensor sensitivity to account for drift by applying the change to the bias voltage at a second time, measuring the currents for a second plurality of time periods, extrapolating to determine the current at the second time, determining the estimated impedance based on the current at the second time, and determining the characteristic of the sensor at the second time based on the estimated impedance at the second time.

Example 21 is an analyte sensor system comprising an analyte sensor sized and shaped for insertion into a host and configured to generate a sensor signal indicative of an analyte concentration level and sensor electronics coupled to the analyte sensor. The sensor electronics are to apply a change to an analyte sensor bias voltage; measure a current value for each of a plurality of time periods after application of the bias voltage change; extrapolate to determine a current at the time of the bias voltage change using the current values for the plurality of time periods; determine an estimated impedance using the determined current at the time of the bias voltage change; determine a characteristic of the analyte sensor using the estimated impedance; receive from the analyte sensor a signal indicative of an analyte concentration; and determine an estimated analyte concentration level using the determined characteristic of the analyte sensor and the received signal.

In Example 22, the subject matter of Example 21 optionally includes the sensor electronics fitting the current values for the plurality of time periods to an exponential curve and extrapolate the fitted curve to determine the current at the time of the bias voltage change.

In Example 23, the subject matter of any one or more of Examples 21-22 optionally includes the sensor electronics determining a sensor sensitivity.

In Example 24, the subject matter of Example 23 optionally includes the sensor electronics updating the sensor sensitivity to account for drift by applying the change to the bias voltage at a second time, measuring the currents for a second plurality of time periods, extrapolating to determine the current at the second time, determining the estimated impedance based on the current at the second time, and determining the characteristic of the sensor at the second time based on the estimated impedance at the second time.

Example 25 is a method of operating an analyte sensor system using sensor electronics. The method comprises applying a change to an analyte sensor bias voltage, measuring a current for one or more time periods after application of the bias voltage change, and determining an estimated impedance based on the current and a double-layer capacitance value. The method also comprises determining a characteristic of the analyte sensor using the estimated impedance, receiving from the analyte sensor a signal indicative of an analyte concentration, and determining an estimated analyte concentration level using the determined characteristic of the analyte sensor and the received signal.

In Example 26, the subject matter of Example 25 optionally includes wherein the double-layer capacitance is a specified double-layer capacitance estimate for the sensor.

In Example 27, the subject matter of any one or more of Examples 25-26 optionally includes increasing the bias voltage and measuring a current response to increasing the bias voltage, decreasing the bias voltage and measuring a current response to decreasing the bias voltage, and determining the double-layer capacitance using the current response to increasing the bias voltage and the current response to decreasing the bias voltage.

In Example 28, the subject matter of any one or more of Examples 25-27 optionally includes measuring currents for a plurality of time periods after changing the bias voltage and determining the double-layer capacitance based on the currents for the plurality of time periods.

Example 29 is an analyte sensor system comprising an analyte sensor sized and shaped for insertion into a host and configured to generate a sensor signal indicative of an analyte concentration level and sensor electronics coupled to the analyte sensor. The sensor electronics are to apply a change to an analyte sensor bias voltage, measure a current for one or more time periods after application of the bias voltage change, and determine an estimated impedance based on the current and a double-layer capacitance value. The sensor electronics are also to determine a characteristic of the analyte sensor using the estimated impedance, receive from the analyte sensor a signal indicative of an analyte concentration, and determine an estimated analyte concentration level using the determined characteristic of the analyte sensor and the received signal.

In Example 30, the subject matter of Example 29 optionally includes wherein the double-layer capacitance is a specified double-layer capacitance estimate for the sensor.

In Example 31, the subject matter of any one or more of Examples 29-30 optionally includes wherein the sensor electronics increase the bias voltage and measuring a current response to increasing the bias voltage, decrease the bias voltage and measure a current response to decreasing the bias voltage, and determine the double-layer capacitance using the current response to increasing the bias voltage and the current response to decreasing the bias voltage.

In Example 32, the subject matter of any one or more of Examples 29-31 optionally includes wherein the sensor electronics measure currents for a plurality of time periods after changing the bias voltage and determine the double-layer capacitance based on the currents for the plurality of time periods.

An example (e.g., "Example 9") of subject matter (e.g., a system or apparatus) may optionally combine any portion or combination of any portion of any one or more of Examples 1-8 to include "means for" performing any portion of any one or more of the functions or methods of Examples 1-8.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments described in the present document.

FIG. 3A is an illustration of an example analyte sensor system.

FIG. 3B is an enlarged view of an example analyte sensor portion of the analyte sensor system shown in FIG. 3A.

FIG. 3C is a cross-sectional view of the analyte sensor of FIG. 3B.

FIG. 8B is a graph that shows two current response curves with the same peak (35 nanoAmps) but a different decay rate.

FIG. 8C is a graph that shows integrated charge for a plurality of equivalent Integral Time periods for two sensors having different decay rates.

FIG. 8D is a graph that shows charge plotted on a logarithmic scale against sample number.

DETAILED DESCRIPTION

Figure 1:
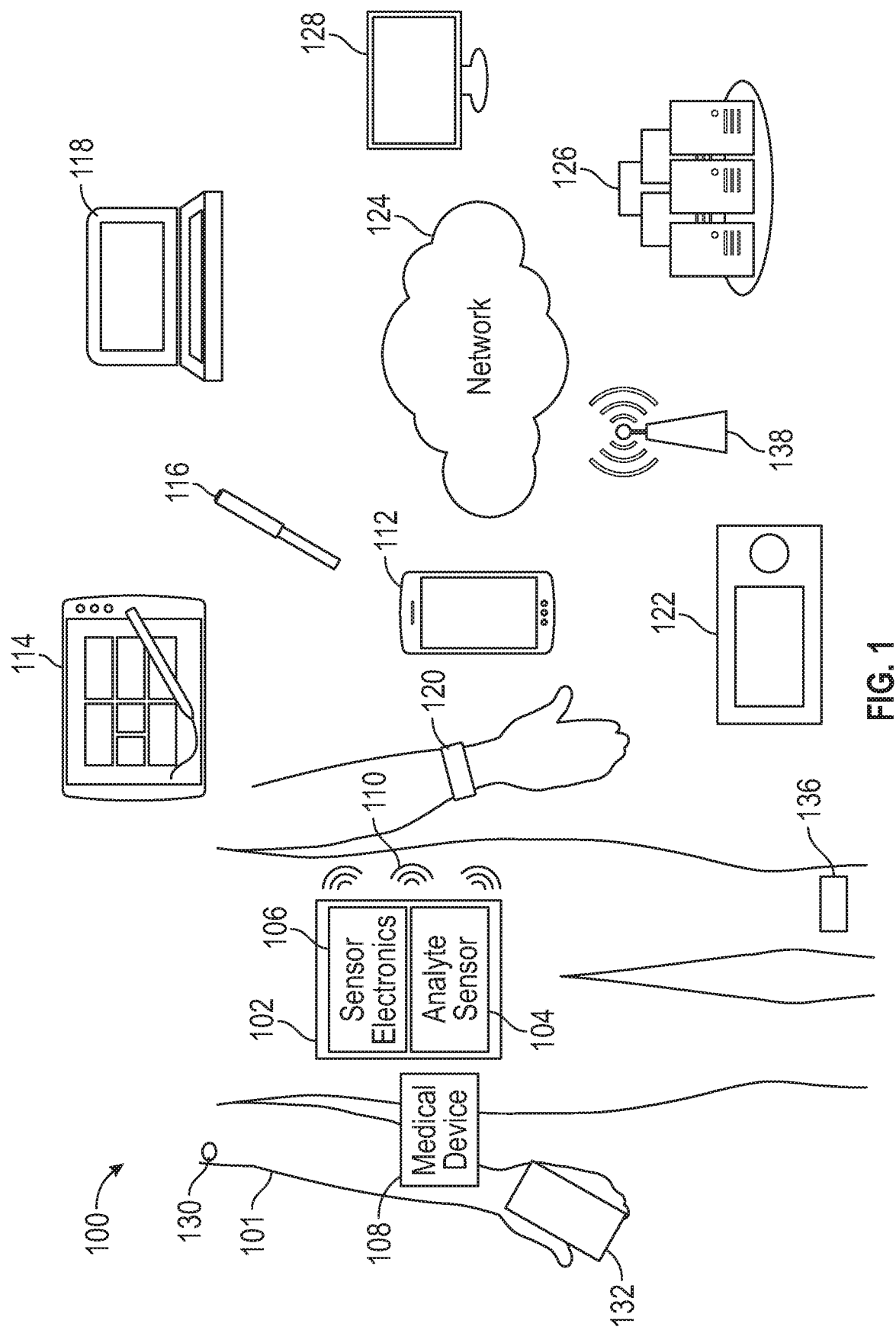
FIG. 1 is an illustration of an example medical device system.

The present inventors have recognized, among other things, that measurements or estimates of impedance in an analyte sensor system may be used to improve the operation of the analyte sensor system. For example, impedance may be used to improve the performance (e.g., accuracy or precision) of an analyte sensor system, or to detect damage or a fault in a sensor. In some examples, an estimate of the impact (e.g., effective capacitance) of a membrane layer interface may be determined.

Overview

An estimate of an impedance of a sensor (e.g., double-layer impedance of a membrane) may be determined using electronic measurements. The impedance estimate may be used, for example, to calibrate a sensor, compensate for drift, identify a damaged sensor, compensate for damage or deviation from a performance standard (e.g., default sensitivity curve).

Impedance may also be used to reduce or eliminate a need for in vivo sensor calibration using blood glucose meter (e.g., "finger stick") data. An analyte sensor, such as a glucose sensor, may be calibrated during manufacture ("factory calibration"), to provide a predictable analyte response curve. For example, a sensor's response to the presence of an analyte (e.g., a glucose concentration) may be checked during (or after) manufacture to assure that the sensor's response to the analyte (e.g., the current signal generated in response to exposure to a known glucose concentration) is within an acceptable range. After implantation in the body, the analyte sensitivity of a sensor is subject to change over time, i.e. "drift." One approach to accounting for in vivo drift is to periodically calibrate the sensor using information from a blood glucose meter (i.e., "finger stick" blood glucose measurements). However, it may be desirable to avoid use of blood glucose meter data or reduce the number or frequency of such in-vivo calibration events. For reasons described in detail below, determining one or more impedance values (e.g., for the circuit 400 shown in FIG. 4) may reduce or eliminate the need to rely on blood glucose meter information. In some examples, impedance may allow for factory calibration, without further in vivo calibration events.

An analyte sensor may include a number of domains or layers, which may include a diffusion resistance domain (e.g., domain 44 shown in FIG. 3C). In a glucose sensor, for example, the diffusion coefficient of electrically neutral glucose molecules in the resistance layer may be a direct correlate or determinant of glucose sensitivity. The electrochemical impedance of the resistance layer is a measure of the mobility of electrically charged ions in the resistance layer. Although the diffusion coefficient and electrochemical impedance are two fundamentally different physical properties associated with two different agents (glucose vs. ions), bench experiments have shown these properties to correlate with each other. As a result, the electrochemical impedance may be used as a surrogate to estimate the diffusion coefficient, which may allow for compensations in in vivo drift of glucose sensitivity. For example, a sensor compensation may be based upon a membrane impedance determined from circuit measurements made in vivo or prior to implantation.

As further described in detail below, the impedance of the membrane (e.g., the electrochemical impedance of the resistance layer) may be determined or estimated based on electrical measurements by sensor electronics or other instrumentation. In various examples, an impedance measurement may be obtained using a sine-wave approach, a step response function approach, or an impulse response function approach. A sine-wave approach may include imposing sinusoidal perturbations in the bias voltage over the RL and measuring the amplitudes of sinusoidal response currents: a scan through a band of frequencies may be performed, and the ratio between the voltage and current excursions may be taken as the impedance at a specific frequency. In step response function approach, a square step change in the bias may be imposed and held, and a perturbation in the sensor current may be measured: the ratio between the Fourier or Laplace transform of the step voltage and that of the transient current is the impedance of the membrane. In an impulse response function approach, a short square wave pulse in the bias voltage may be imposed, and a perturbation in the sensor current may be measured. The impedance may be determined from the current perturbation and the applied bias voltage pulse.

The sensor sensitivity ($m_t$) correlates linearly with the reciprocal of the membrane impedance (ZRL,t), i.e. ZRL, $t*m_t$=constant. This relationship can be employed to make use of impedance for estimating in vivo sensitivity in real time:

$$\hat{m}_t = Z_{RL,t}^{-1} \cdot \text{constant}$$

Based on this relationship, a sensor may be calibrated in vivo, which may allow for compensation for drift after deployment in a host.

In some examples, a sensor elapsed time (t) since insertion and an impedance ($R_t$) determined from measurements at the elapsed time may be used as input for a function to estimate sensitivity, e.g., sensitivity ($m_t$) of the sensor may be provided by the function $m_t = f(t)/R_t$. In some examples, an initial calibration curve (CC) may also be used to determine an estimated sensor sensitivity, e.g., $m_t = f(CC, t)/R_t$.

An estimated sensor sensitivity may be used to determine an estimated analyte concentration (e.g., estimated glucose concentration) based upon sensor output (e.g., a current or charge count from a working electrode measured using sensor electronics) and the sensor sensitivity ($m_t$) estimated using the impedance.

Testing and experimentation have been conducted to establish and verify techniques for improving performance of analyte sensor systems, mitigating the effect of double-layer capacitance effects, and detecting, quantifying, or compensating for damage or abnormalities in a sensor membrane. Data, charts, and examples are provided to assist with describing the present subject matter.

Impedance characteristics of a sensor may be used to detect or determine (e.g., quantify) an amount of damage or manufacturing abnormality (e.g., membrane imperfection) in a sensor. A sensor may be functional even though a membrane may include minor imperfections that may be identifiable under a microscope. Some sensors with extensive damage or major manufacturing abnormalities may provide unacceptable performance. Identification of such sensors may provide an opportunity to remove a sensor from circulation or compensate an estimated analyte concentration based on an understanding of impedance characteristics of the sensor. In some examples, a combination of characteristics may be used to assess the integrity of a sensor membrane, e.g., to identify sensors with damage or abnormality, or characterize the extent of sensor abnormality or damage. For example, impedance may be used in combination with dual frequency impedance (e.g., impedance 100 Hz and 1000 Hz), or impedance may be used in combination with an impedance trend or time-based variable (e.g., impedance difference at different points in time), or impedance difference at different frequencies may be used in combination with impedance difference at different points in time (e.g., 72 seconds and 180 seconds or low point and a stable point.) In other examples, other variables, such as signal variability (e.g., perceived noise level), or response to a voltage change (e.g., rate of impedance change) may also be used in combination with any of the above factors and combinations.

In certain situations, such as accidently bumping an analyte sensor, catching a sensor base on an object, or "tenting" of an adhesive patch (e.g., when portions of the adhesive patch are not completely adhered to the skin) to which a sensor is attached, an analyte sensor may be partially pulled out of the skin or otherwise dislodged, which may result in an inaccurate sensor reading. Such an event may be detected based upon a change in impedance.

Sensor impedance may depend on the insertion depth of the sensor into a host. If a sensor is retracted a significant distance, a step change in sensor impedance may be observed.

In an example, an impedance may be measured after insertion, and subsequently measured after insertion. For example, the impedance may be measured recurrently, or may be measured responsive to detection of an event, such as a potential dislodgement event, which may for example be detected using an accelerometer in sensor electronics, or from other sensor information. A sudden change in impedance may indicate dislodgment. For example, a determined impedance change greater than a predetermined impedance change (e.g., in ohms) over a predetermined time period may indicate a dislodgement event. In some examples, a system may declare an alert or raise a "replace sensor" alarm" responsive to detection of a sudden change in impedance.

In some examples, factory calibration may be improved by using impedance for factory calibration. Impedance may be used to determine a calibration value or curve for a sensor, or verification that a sensitivity of the sensor is within acceptable limits. Without use of impedance, calibration may require sequentially exposing a sensor to immersion in fluid baths having varying levels of analyte concentration (e.g., varying glucose concentrations), while applying a bias potential, which may be complicated, time consuming, expensive, or difficult to scale. In some examples, impedance may be used as a replacement (or compliment) to such soaking in analyte solutions.

In an example, a sensor may be pre-soaked in a solution to facilitate measurement of impedance. An impedance measurement may then be made. In an example, the impedance determination (e.g., using current measurements described above) may take one minute, or less, in contrast to a typical one-hour measurement process of current measurements in response to analyte concentrations. This approach may be desirable, for example, because the process does not require application of a bias potential, and a large number of sensors may be soaked simultaneously. In an example, an eight-channel potentiostat may be used to simultaneously measure the impedance of eight sensors on a single fixture. In some examples, the determined impedance values may be used to determine a sensor sensitivity or confirm that the sensor sensitivity or impedance is within defined limits, or to predict drift or later estimate in vivo drift, e.g., using in vivo impedance determinations, which may be compared to the factory impedance values or a default value or range.

In some examples, a sensor may be pre-screened using an impedance procedure, so that damaged sensors may be identified and removed from a production process, which may improve sensor accuracy statistics (e.g., reduce MARD), or improve process efficiency by reducing the number of sensors that proceed through a conventional bath calibration process.

Example System

FIG. 1 is an illustration of an example system 100. The system 100 may include an analyte sensor system 102 that may be coupled to a host 101. The host 101 may be a human patient. The patient may, for example, be subject to a temporary or permanent diabetes condition or other health condition for which analyte monitoring may be useful.

The analyte sensor system 102 may include an analyte sensor 104, which may for example be a glucose sensor. The glucose sensor may be any device capable of measuring the concentration of glucose. For example, the analyte sensor 104 may be fully implantable, or the analyte sensor 104 may be wearable on the body (e.g., on the body but not under the skin), or the analyte sensor 104 may be a transcutaneous device (e.g., with a sensor residing under or in the skin of a host). It should be understood that the devices and methods described herein can be applied to any device capable of detecting a concentration of glucose and providing an output signal that represents the concentration of glucose (e.g., as a form of analyte data).

The analyte sensor system 102 may also include sensor electronics 106. In some examples, the analyte sensor 104 and sensor electronics 106 may be provided as an integrated package. In other examples, the analyte sensor 104 and sensor electronics 106 may be provided as separate components or modules. For example, the analyte sensor system 102 may include a disposable (e.g., single-use) base that may include the analyte sensor 104, a component for attaching the sensor 104 to a host (e.g., an adhesive pad), or a mounting structure configured to receive another component. The system 102 may also include a sensor electronics package, which may include some or all of the sensor electronics 106 shown in FIG. 2. The sensor electronics package may be reusable.

An analyte sensor 104 may use any known method, including invasive, minimally-invasive, or non-invasive sensing techniques (e.g., optically excited fluorescence, microneedle, transdermal monitoring of glucose), to provide a data stream indicative of the concentration of the analyte in a host 101. The data stream may be a raw data signal, which may be converted into a calibrated and/or filtered data stream that is used to provide a useful value of the analyte (e.g., estimated blood glucose concentration level) to a user, such as a patient or a caretaker (e.g., a parent, a relative, a guardian, a teacher, a doctor, a nurse, or any other individual that has an interest in the wellbeing of the host 101).

Analyte sensor 104 may, for example, be a continuous glucose sensor, which may, for example, include a subcutaneous, transdermal (e.g., transcutaneous), or intravascular device. In some embodiments, such a sensor or device may recurrently (e.g., periodically or intermittently) analyze sensor data. The glucose sensor may use any method of glucose measurement, including enzymatic, chemical, physical, electrochemical, spectrophotometric, polarimetric, calorimetric, iontophoretic, radiometric, immunochemical, and the like. In various examples, the analyte sensor system 102 may be or include a continuous glucose monitor sensor available from DexCom™, (e.g., the DexCom G5™ sensor or Dexcom G6™ sensor or any variation thereof), from Abbott™ (e.g., the Libre™ sensor), or from Medtronic™ (e.g., the Enlite™ sensor).

In some examples, analyte sensor 104 may be an implantable glucose sensor, such as described with reference to U.S. Pat. No. 6,001,067 and U.S. Patent Publication No. US-2005-0027463-A1, which are incorporated by reference. In some examples, analyte sensor 104 may be a transcutaneous glucose sensor, such as described with reference to U.S. Patent Publication No. US-2006-0020187-A1, which is incorporated by reference. In some examples, analyte sensor 104 may be configured to be implanted in a host vessel or extracorporeally, such as is described in U.S. Patent Publication No. US-2007-0027385-A1, co-pending U.S. Patent Publication No. US-2008-0119703-A1 filed Oct. 4, 2006, U.S. Patent Publication No. US-2008-0108942-A1 filed on Mar. 26, 2007, and U.S. Patent Application No. US-2007-0197890-A1 filed on Feb. 14, 2007, all of which are incorporated by reference. In some examples, the continuous glucose sensor may include a transcutaneous sensor such as described in U.S. Pat. No. 6,565,509 to Say et al., which is incorporated by reference. In some examples, analyte sensor 104 may be a continuous glucose sensor that includes a subcutaneous sensor such as described with reference to U.S. Pat. No. 6,579,690 to Bonnecaze et al. or U.S. Pat. No. 6,484,046 to Say et al., which are incorporated by reference. In some examples, the continuous glucose sensor may include a refillable subcutaneous sensor such as described with reference to U.S. Pat. No. 6,512,939 to Colvin et al., which is incorporated by reference. The continuous glucose sensor may include an intravascular sensor such as described with reference to U.S. Pat. No. 6,477,395 to Schulman et al., which is incorporated by reference. The continuous glucose sensor may include an intravascular sensor such as described with reference to U.S. Pat. No. 6,424,847 to Mastrototaro et al., which is incorporated by reference.

The system 100 may also include a second medical device 108, which may, for example, be a drug delivery device (e.g., insulin pump or insulin pen). In some examples, the medical device 108 may be or include a sensor, such as another analyte sensor 104, a heart rate sensor, a respiration sensor, a motion sensor (e.g. accelerometer), posture sensor (e.g. 3-axis accelerometer), acoustic sensor (e.g. to capture ambient sound or sounds inside the body). In some examples, medical device 108 may be wearable, e.g., on a watch, glasses, contact lens, patch, wristband, ankle band, or other wearable item, or may be incorporated into a handheld device (e.g., a smartphone). In some examples, the medical device 108 may include a multi-sensor patch that may, for example, detect one or more of an analyte level (e.g., glucose, lactate, insulin or other substance), heart rate, respiration (e.g., using impedance), activity (e.g., using an accelerometer), posture (e.g., using an accelerometer), galvanic skin response, tissue fluid levels (e.g., using impedance or pressure).

The analyte sensor system 102 may communicate with the second medical device 108 via a wired connection, or via a wireless communication signal 110. For example, the analyte sensor system 102 may be configured to communicate using via radio frequency (e.g., Bluetooth, Medical Implant Communication System (MICS), Wi-Fi, NFC, RFID, Zigbee, Z-Wave or other communication protocols), optically (e.g., infrared), sonically (e.g., ultrasonic), or a cellular protocol (e.g., CDMA (Code Division Multiple Access) or GSM (Global System for Mobiles)), or via a wired connection (e.g., serial, parallel, etc.).

The system 100 may also include a wearable sensor 130, which may include a sensor circuit (e.g., a sensor circuit configured to detect a glucose concentration or other analyte concentration) and a communication circuit, which may, for example, be a near field communication (NFC) circuit. In some examples, information from the wearable sensor 130 may be retrieved from the wearable sensor 130 using a user device 132 such as a smart phone that is configured to communicate with the wearable sensor 130 via NFC when the user device 132 is placed near the wearable sensor 130 (e.g., swiping the user device 132 over the sensor 130 retrieves sensor data from the wearable sensor 130 using NFC). The use of NFC communication may reduce power consumption by the wearable sensor 130, which may reduce the size of a power source (e.g., battery or capacitor) in the wearable sensor 130 or extend the usable life of the power source. In some examples, the wearable sensor 130 may be wearable on an upper arm as shown. In some examples, a wearable sensor 130 may additionally or alternatively be on the upper torso of the patient (e.g., over the heart or over a lung), which may, for example, facilitate detecting heart rate, respiration, or posture. A wearable sensor 136 may also be on the lower body (e.g., on a leg).

In some examples, an array or network of sensors may be associated with the patient. For example, one or more of the analyte sensor system 102, medical device 108, wearable device 120 such as a watch, and an additional wearable sensor 130 may communicate with one another via wired or wireless (e.g., Bluetooth, MICS, NFC or any of the other options described above,) communication. The additional wearable sensor 130 may be any of the examples described above with respect to medical device 108. The analyte sensor system 102, medical device 108, and additional sensor 130 on the host 101 are provided for the purpose of illustration and description and are not necessarily drawn to scale.

The system 100 may also include one or more peripheral devices, such as a hand-held smart device (e.g., smartphone) 112, tablet 114, smart pen 116 (e.g., insulin delivery pen with processing and communication capability), computer 118, a wearable device 120 such as a watch, or peripheral medical device 122 (which may be a proprietary device such as a proprietary user device available from DexCom), any of which may communicate with the analyte sensor system 102 via a wireless communication signal 110, and may also communicate over a network 124 with a server system (e.g., remote data center) 126 or with a remote terminal 128 to facilitate communication with a remote user (not shown) such as a technical support staff member or a clinician.

The wearable device 120 may include an activity sensor, a heart rate monitor (e.g., light-based sensor or electrode-based sensor), a respiration sensor (e.g., acoustic- or electrode-based), a location sensor (e.g., GPS), or other sensors.

The system 100 may also include a wireless access point (WAP) 138 that may be used to communicatively couple one or more of analyte sensor system 102, network 124, server system 126, medical device 108 or any of the peripheral devices described above. For example, WAP 138 may provide Wi-Fi and/or cellular connectivity within system 100. Other communication protocols (e.g., Near Field Communication (NFC) or Bluetooth) may also be used among devices of the system 100. In some examples, the server system 126 may be used to collect analyte data from analyte sensor system 102 and/or the plurality of other devices, and to perform analytics on collected data, generate or apply universal or individualized models for glucose levels, and communicate such analytics, models, or information based thereon back to one or more of the devices in the system 100.

Figure 2:
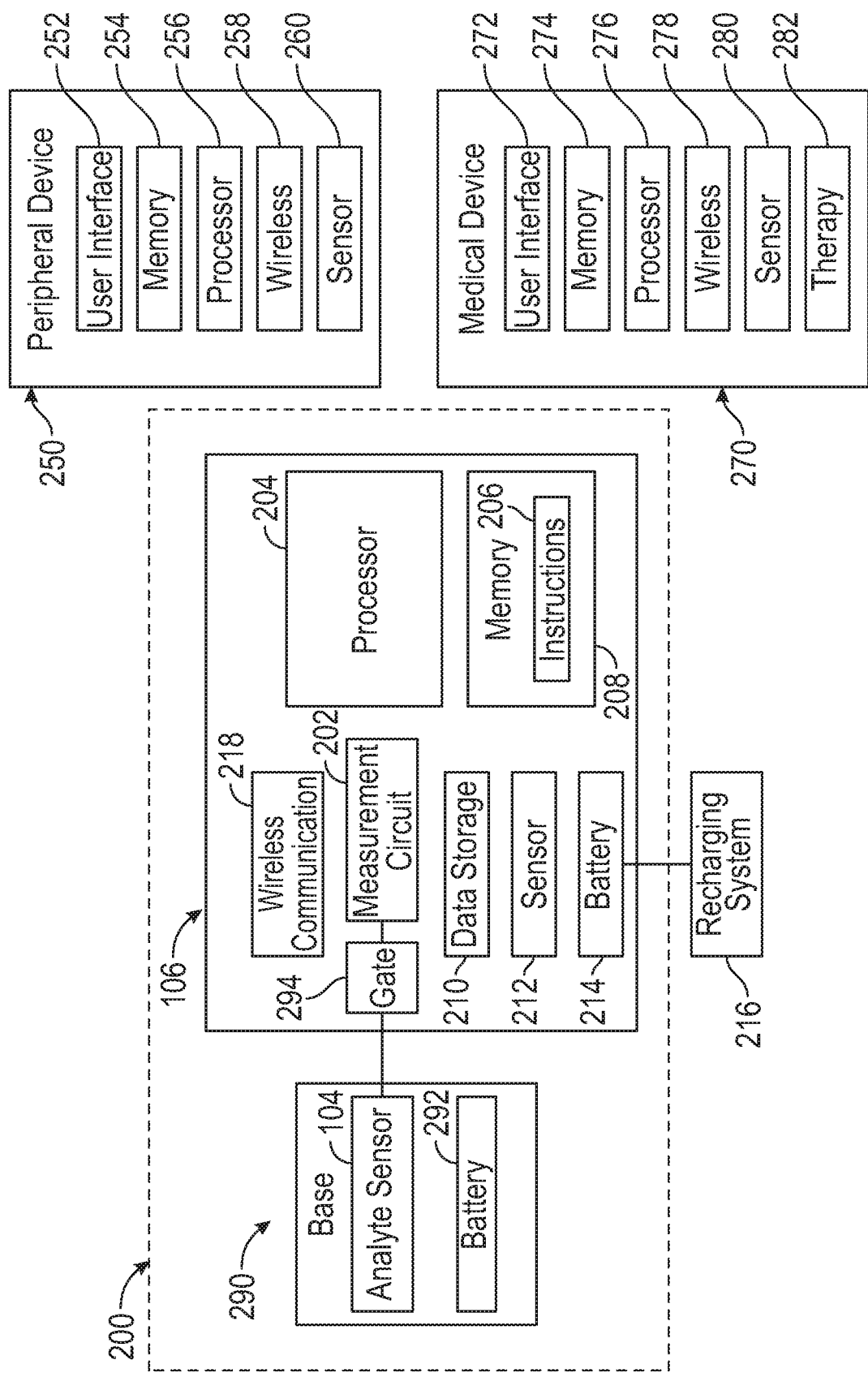
FIG. 2 is a schematic illustration of various example electronic components that may be part of the medical device system shown in FIG. 1.

FIG. 2 is a schematic illustration of various example electronic components that may be part of a medical device system 200. In an example, the system 200 may include sensor electronics 106 and a base 290. While a specific example of division of components between the base 290 and sensor electronics 106 is shown, it is understood that some examples may include additional components in the base 290 or in the sensor electronics 106, and that some of the components (e.g., a battery or supercapacitor) that are shown in the sensor electronics 106 may be alternatively or additionally (e.g., redundantly) provided in the base 290.

In an example, the base 290 may include the analyte sensor 104 and a battery 292. In some examples, the base 290 may be replaceable, and the sensor electronics 106 may include a debouncing circuit (e.g., gate with hysteresis or delay) to avoid, for example, recurrent execution of a power-up or power down process when a battery is repeatedly connected and disconnected or avoid processing of noise signal associated with removal or replacement of a battery.

The sensor electronics 106 may include electronics components that are configured to process sensor information, such as sensor data, and generate transformed sensor data and displayable sensor information. The sensor electronics 106 may, for example, include electronic circuitry associated with measuring, processing, storing, or communicating continuous analyte sensor data, including prospective algorithms associated with processing and calibration of the sensor data. The sensor electronics 106 may include hardware, firmware, and/or software that enables measurement of levels of the analyte via a glucose sensor. Electronic components may be affixed to a printed circuit board (PCB), or the like, and can take a variety of forms. For example, the electronic components may take the form of an integrated circuit (IC), such as an Application-Specific Integrated Circuit (ASIC), a microcontroller, and/or a processor.

As shown in FIG. 2, the sensor electronics 106 may include a measurement circuit 202 (e.g., potentiostat), which may be coupled to the analyte sensor 104 and configured to recurrently obtain analyte sensor readings using the analyte sensor 104, for example by continuously or recurrently measuring a current flow indicative of analyte concentration. The sensor electronics 106 may include a gate circuit 294, which may be used to gate the connection between the measurement circuit 202 and the analyte sensor 104. In an example, the analyte sensor 104 accumulates charge over an accumulation period, and the gate circuit 294 is opened so that the measurement circuit 202 can measure the accumulated charge. Gating the analyte sensor 104 may improve the performance of the sensor system 102 by creating a larger signal to noise or interference ratio (e.g., because charge accumulates from an analyte reaction, but sources of interference, such as the presence of acetaminophen near a glucose sensor, do not accumulate, or accumulate less than the charge from the analyte reaction). The sensor electronics 106 may also include a processor 204, which may retrieve instructions 206 from memory 208 and execute the instructions 206 to determine control application of bias potentials to the analyte sensor 104 via the potentiostat, interpret signals from the sensor 104, or compensate for environmental factors. The processor 204 may also save information in data storage memory 210 or retrieve information from data storage memory 210. In various examples, data storage memory 210 may be integrated with memory 208, or may be a separate memory circuit, such as a non-volatile memory circuit (e.g., flash RAM). Examples of systems and methods for processing sensor analyte data are described in more detail herein and in U.S. Pat. Nos. 7,310,544 and 6,931,327.

The sensor electronics 106 may also include a sensor 212, which may be coupled to the processor 204. The sensor 212 may be a temperature sensor, accelerometer, or another suitable sensor. The sensor electronics 106 may also include a power source such as a capacitor or battery 214, which may be integrated into the sensor electronics 106, or may be removable, or part of a separate electronics package. The battery 214 (or other power storage component, e.g., capacitor) may optionally be rechargeable via a wired or wireless (e.g., inductive or ultrasound) recharging system 216. The recharging system 216 may harvest energy or may receive energy from an external source or on-board source. In various examples, the recharge circuit may include a triboelectric charging circuit, a piezoelectric charging circuit, an RF charging circuit, a light charging circuit, an ultrasonic charging circuit, a heat charging circuit, a heat harvesting circuit, or a circuit that harvests energy from the communication circuit. In some examples, the recharging circuit may recharge the rechargeable battery using power supplied from a replaceable battery (e.g., a battery supplied with a base component).

The sensor electronics 106 may also include one or more supercapacitors in the sensor electronics package (as shown), or in the base 290. For example, the supercapacitor may allow energy to be drawn from the battery 214 in a highly consistent manner to extend the life of the battery 214. The battery 214 may recharge the supercapacitor after the supercapacitor delivers energy to the communication circuit or to the processor 204, so that the supercapacitor is prepared for delivery of energy during a subsequent high-load period. In some examples, the supercapacitor may be configured in parallel with the battery 214. A device may be configured to preferentially draw energy from the supercapacitor, as opposed to the battery 214. In some examples, a supercapacitor may be configured to receive energy from a rechargeable battery for short-term storage and transfer energy to the rechargeable battery for long-term storage.

The supercapacitor may extend an operational life of the battery 214 by reducing the strain on the battery 214 during the high-load period. In some examples, a supercapacitor removes at least 10% of the strain off the battery during high-load events. In some examples, a supercapacitor removes at least 20% of the strain off the battery during high-load events. In some examples, a supercapacitor removes at least 30% of the strain off the battery during high-load events. In some examples, a supercapacitor removes at least 50% of the strain off the battery during high-load events.

The sensor electronics 106 may also include a wireless communication circuit 218, which may for example include a wireless transceiver operatively coupled to an antenna. The wireless communication circuit 218 may be operatively coupled to the processor 204 and may be configured to wirelessly communicate with one or more peripheral devices or other medical devices, such as an insulin pump or smart insulin pen.

A peripheral device 250 may, for example, be a wearable device (e.g., activity monitor), such as a wearable device 120. In other examples, the peripheral device 250 may be a hand-held smart device 112 (e.g., smartphone or other device such as a proprietary handheld device available from Dexcom), a tablet 114, a smart pen 116, or special-purpose computer 118 shown in FIG. 1.

The peripheral device 250 may include a user interface 252, a memory circuit 254, a processor 256, a wireless communication circuit 258, a sensor 260, or any combination thereof. The peripheral device 250 may also include a power source, such as a battery. The peripheral device 250 may not necessarily include all of the components shown in FIG. 2. The user interface 252 may, for example, include a touch-screen interface, a microphone (e.g., to receive voice commands), or a speaker, a vibration circuit, or any combination thereof, which may receive information from a user (e.g., glucose values) or deliver information to the user such as glucose values, glucose trends (e.g., an arrow, graph, or chart), or glucose alerts. The processor 256 may be configured to present information to a user, or receive input from a user, via the user interface 252. The processor 256 may also be configured to store and retrieve information, such as communication information (e.g., pairing information or data center access information), user information, sensor data or trends, or other information in the memory circuit 254. The wireless communication circuit 258 may include a transceiver and antenna configured to communicate via a wireless protocol, such as Bluetooth, MICS, or any of the other options described above. The sensor 260 may, for example, include an accelerometer, a temperature sensor, a location sensor, biometric sensor, or blood glucose sensor, blood pressure sensor, heart rate sensor, respiration sensor, or other physiologic sensor. The peripheral device 250 may, for example, be a hand-held smart device 112 (e.g., smartphone or other device such as a proprietary handheld device available from Dexcom), tablet 114, smart pen 116, watch or other wearable device 120, or computer 118 shown in FIG. 1.

The peripheral device 250 may be configured to receive and display sensor information that may be transmitted by sensor electronics 106 (e.g., in a customized data package that is transmitted to the display devices based on their respective preferences). Sensor information (e.g., blood glucose concentration level) or an alert or notification (e.g., "high glucose level", "low glucose level" or "fall rate alert" may be communicated via the user interface 252 (e.g., via visual display, sound, or vibration). In some examples, the peripheral device 250 may be configured to display or otherwise communicate the sensor information as it is communicated from the sensor electronics 106 (e.g., in a data package that is transmitted to respective display devices). For example, the peripheral device 250 may transmit data that has been processed (e.g., an estimated analyte concentration level that may be determined by processing raw sensor data), so that a device that receives the data may not be required to further process the data to determine usable information (such as the estimated analyte concentration level). In other examples, the peripheral device 250 may process or interpret the received information (e.g., to declare an alert based on glucose values or a glucose trend). In various examples, the peripheral device 250 may receive information directly from sensor electronics 106, or over a network (e.g., via a cellular or Wi-Fi network that receives information from the sensor electronics 106 or from a device that is communicatively coupled to the sensor electronics 106).

Referring again to FIG. 2, the medical device 270 may include a user interface 272, a memory circuit 274, a processor 276, a wireless communication circuit 278, a sensor 280, a therapy circuit 282, or any combination thereof. The user interface 272 may, for example, include a touch-screen interface, a microphone, or a speaker, a vibration circuit, or any combination thereof, which may receive information from a user (e.g., glucose values, alert preferences, calibration coding) or deliver information to the user, such as e.g., glucose values, glucose trends (e.g., an arrow, graph, or chart), or glucose alerts. The processor 276 may be configured to present information to a user, or receive input from a user, via the user interface 272. The processor 276 may also be configured to store and retrieve information, such as communication information (e.g., pairing information or data center access information), user information, sensor data or trends, or other information in the memory circuit 274. The wireless communication circuit 278 may include a transceiver and antenna configured communicate via a wireless protocol, such as Bluetooth, Medical Implant Communication System (MICS), Wi-Fi, Zigbee, or a cellular protocol (e.g., CDMA (Code Division Multiple Access) or GSM (Global System for Mobiles)). The sensor 280 may, for example, include an accelerometer, a temperature sensor, a location sensor, biometric sensor, or blood glucose sensor, blood pressure sensor, heart rate sensor, respiration sensor, or other physiologic sensor. The medical device 270 may include two or more sensors (or memories or other components), even though only one sensor 280 is shown in the example in FIG. 2. In various examples, the medical device 270 may be a smart handheld glucose sensor (e.g., blood glucose meter), drug pump (e.g., insulin pump), or other physiologic sensor device, therapy device, or combination thereof. In various examples, the medical device 270 may be the medical device 108, peripheral medical device 122, wearable device 120, wearable sensor 130, or wearable sensor 136 shown in FIG. 1.

In examples where the peripheral medical device 122 or medical device 270 is an insulin pump, the pump and analyte sensor system 102 may be in two-way communication (e.g., so the pump can request a change to an analyte transmission protocol, e.g., request a data point or request data on a more frequent schedule), or the pump and analyte sensor system 102 may communicate using one-way communication (e.g., the pump may receive analyte concentration level information from the analyte sensor system). In one-way communication, a glucose value may be incorporated in an advertisement message, which may be encrypted with a previously-shared key. In a two-way communication, a pump may request a value, which the analyte sensor system 102 may share, or obtain and share, in response to the request from the pump, and any or all of these communications may be encrypted using one or more previously-shared keys. An insulin pump may receive and track analyte (e.g., glucose) values transmitted from analyte sensor system 102 using one-way communication to the pump for one or more of a variety of reasons. For example, an insulin pump may suspend or activate insulin administration based on a glucose value being below or above a threshold value.

In some examples, the system 100 shown in FIG. 1 may include two or more peripheral devices that each receives information directly or indirectly from the analyte sensor system 102. Because different display devices provide many different user interfaces, the content of the data packages (e.g., amount, format, and/or type of data to be displayed, alarms, and the like) may be customized (e.g., programmed differently by the manufacturer and/or by an end user) for each particular device. For example, in the embodiment of FIG. 1, a plurality of different peripheral devices may be in direct wireless communication with a sensor electronics module (e.g., such as an on-skin sensor electronics 106 that is physically connected to the continuous analyte sensor 104) during a sensor session to enable a plurality of different types and/or levels of display and/or functionality associated with the displayable sensor information, or, to save battery power in the sensor system 102, one or more specified devices may communicate with the analyte sensor system 102 and relay (i.e., share) information to other devices directly or through a server system (e.g., a network-connected data center) 126.

FIG. 3A is a side view of an analyte sensor system, illustrating an analyte sensor 34 implanted into a host. A mounting unit 14 may be adhered to the host's skin using an adhesive pad 8. The adhesive pad 8 may be formed from an extensible material, which may be removably attached to the skin using an adhesive. The sensor electronics 106 may mechanically couple to the adhesive pad 8.

FIG. 3B is an enlarged view of a distal portion of the analyte sensor 34. The analyte sensor 34 may be adapted for insertion under the host's skin and may be mechanically coupled to the mounting unit 14 and electrically coupled to the sensor electronics 106. The example analyte sensor 34 shown in FIG. 3B includes an elongated conductive body 41. The elongated conductive body 41 can include a core with various layers positioned thereon. A first layer 38 that at least partially surrounds the core and includes a working electrode, for example located in window 39). In some examples, the core and the first layer 38 are made of a single material (such as, for example, platinum). In some examples, the elongated conductive body 41 is a composite of two conductive materials, or a composite of at least one conductive material and at least one non-conductive material. A membrane system 32 is located over the working electrode and may cover other layers and/or electrodes of the sensor 34, as described herein.

The first layer 38 may be formed of a conductive material. The working electrode (at window 39) is an exposed portion of the surface of the first layer 38. Accordingly, the first layer 38 is formed of a material configured to provide a suitable electroactive surface for the working electrode. Examples of suitable materials include, but are not limited to, platinum, platinum-iridium, gold, palladium, iridium, graphite, carbon, a conductive polymer, an alloy, and/or the like.

A second layer 40 surrounds at least a portion of the first layer 38, thereby defining boundaries of the working electrode. In some examples, the second layer 40 serves as an insulator and is formed of an insulating material, such as polyimide, polyurethane, parylene, or any other suitable insulating materials or materials. In some examples, the second layer 40 is configured such that the working electrode (of the layer 38) is exposed via the window 39.

In some examples, the sensor 34 further includes a third layer 43 comprising a conductive material. The third layer 43 may comprise a reference electrode. In some examples, the third layer 43, including the reference electrode, is formed of a silver-containing material that is applied onto the second layer 40 (e.g., an insulator). The silver-containing material may include various materials and be in various forms such as, for example, Ag/AgCl-polymer pasts, paints, polymer-based conducting mixtures, inks, etc.

The analyte sensor 34 may include two (or more) electrodes, e.g., a working electrode at the layer 38 and exposed at window 39 and at least one additional electrode, such as a reference electrode of the layer 43. In the example arrangement of FIG. 1B, the reference electrode also functions as a counter electrode, although other arrangements can include a separate counter electrode. While the analyte sensor 34 may be used with a mounting unit in some examples, in other examples, the analyte sensor 34 may be used with other types of sensor systems. For example, the analyte sensor 34 may be part of a system that includes a battery and sensor in a single package, and may optionally include, for example, a near-field communication (NFC) circuit.

FIG. 3C is a cross-sectional view through the sensor 34 of FIG. 3B on plane 2-2 illustrating a membrane system 32. The membrane system 32 may include a number of domains (e.g., layers). In an example, the membrane system 32 may include an enzyme domain 42, a diffusion resistance domain 44, and a bioprotective domain 46 located around the working electrode. In some examples, a unitary diffusion resistance domain and bioprotective domain may be included in the membrane system 32 (e.g., wherein the functionality of both the diffusion resistance domain and bioprotective domain are incorporated into one domain).

The membrane system 32, in some examples, also includes an electrode layer 47. The electrode layer 47 may be arranged to provide an environment between the surfaces of the working electrode and the reference electrode that facilitates the electrochemical reaction between the electrodes. For example, the electrode layer 47 may include a coating that maintains a layer of water at the electrochemically reactive surfaces of the sensor 34.

In some examples, the sensor 34 may be configured for short-term implantation (e.g., from about 1 to 30 days). However, it is understood that the membrane system 32 can be modified for use in other devices, for example, by including only one or more of the domains, or additional domains. For example, a membrane system may include a plurality of resistance layers, or a plurality of enzyme layers. In some example, the resistance domain 44 may include a plurality of resistance layers, or the enzyme domain 42 may include a plurality of enzyme layers.

The diffusion resistance domain 44 may include a semipermeable membrane that controls the flux of oxygen and glucose to the underlying enzyme domain 42. As a result, the upper limit of linearity of glucose measurement is extended to a much higher value than that which is achieved without the diffusion resistance domain 44.

In some examples, the membrane system 32 may include a bioprotective domain 46, also referred to as a domain or biointerface domain, comprising a base polymer as described in more detail elsewhere herein. However, the membrane system 32 of some examples can also include a plurality of domains or layers including, for example, an electrode domain, an interference domain, or a cell disruptive domain, such as described in more detail elsewhere herein and in U.S. Pat. Nos. 7,494,465, 8,682,408, and 9,044,199, which are incorporated herein by reference in their entirety.

It is to be understood that sensing membranes modified for other sensors, for example, may include fewer or additional layers. For example, in some examples, the membrane system 32 may comprise one electrode layer, one enzyme layer, and two bioprotective layers, but in other examples, the membrane system 32 may comprise one electrode layer, two enzyme layers, and one bioprotective layer. In some examples, the bioprotective layer may be configured to function as the diffusion resistance domain 44 and control the flux of the analyte (e.g., glucose) to the underlying membrane layers.

In some examples, one or more domains of the sensing membranes may be formed from materials such as silicone, polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, poly(ethylene oxide), poly(propylene oxide) and copolymers and blends thereof, polysulfones and block copolymers thereof including, for example, di-block, tri-block, alternating, random and graft copolymers.

In some examples, the sensing membrane can be deposited on the electroactive surfaces of the electrode material using known thin or thick film techniques (for example, spraying, electro-depositing, dipping, or the like). The sensing membrane located over the working electrode does not have to have the same structure as the sensing membrane located over the reference electrode 30; for example, the enzyme domain 42 deposited over the working electrode does not necessarily need to be deposited over the reference or counter electrodes.

Although the examples illustrated in FIGS. 3B-3C involve circumferentially extending membrane systems, the membranes described herein may be applied to any planar or non-planar surface, for example, the substrate-based sensor structure of U.S. Pat. No. 6,565,509 to Say et al., which is incorporated by reference.

In an example in which the analyte sensor 34 is a glucose sensor, glucose analyte can be detected utilizing glucose oxidase, which produces hydrogen peroxide ($H_2O_2$) as a byproduct of the reaction of glucose with glucose oxidase. The hydrogen peroxide reacts with the surface of the working electrode, producing two protons ($2H^+$), two electrons ($2e^-$) and one molecule of oxygen ($O_2$), which produces an electronic current that may be detected by the sensor electronics 106. The amount of current is a function of the glucose concentration level. A calibration curve may be used to provide an estimated glucose concentration level based on a measured current. The amount of current is also a function of the diffusivity of glucose through the sensor membrane. The glucose diffusivity may change over time, which may cause the sensor glucose sensitivity to change over time, or "drift."

Figure 4:
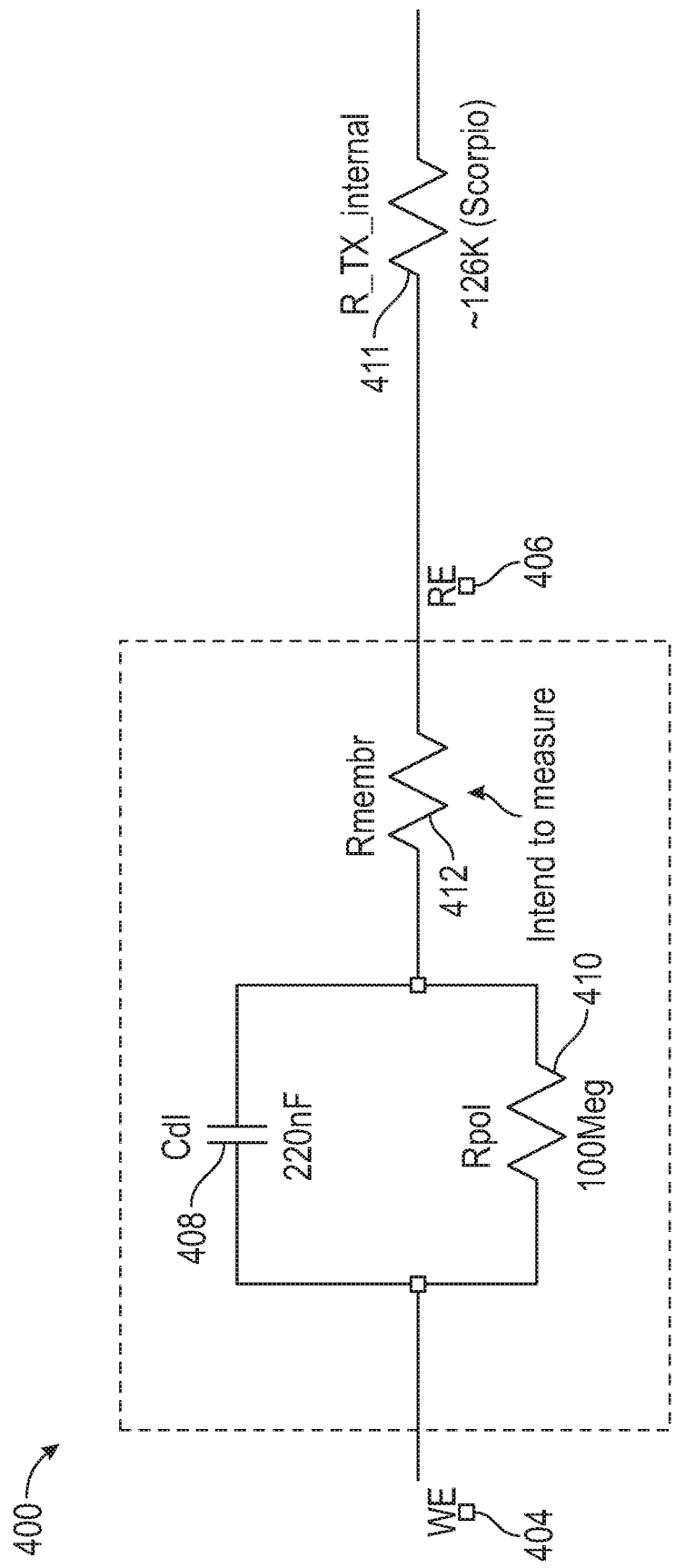
FIG. 4 is a schematic illustration of a circuit that represents the behavior of an analyte sensor.

FIG. 4 is a schematic illustration of a circuit 400 that represents the behavior of an analyte sensor, such as the sensor 34 shown in FIGS. 3A-3C. As described above, the interaction of hydrogen peroxide (generated from the interaction between glucose analyte and glucose oxidase) and working electrode (WE) 404 produces a voltage differential between the working electrode (WE) 404 and reference electrode (RE) 406, which drives a current that may be measured by sensor electronics 106 and used to estimate a glucose concentration level. The circuit 400 also includes a double-layer capacitance (Cdl) 408, which occurs at an interface between the working electrode (WE) 404 and the adjacent membrane (not shown, see description above).

In a typical in vivo analyte sensor, a double-layer capacitance (Cdl) may occur at the interface between the working electrode 404 and the adjacent membrane due to the presence (e.g., during application of an applied voltage between the working electrode 404 and reference electrode) of two layers of ions with opposing polarity. The equivalent circuit 400 may also include a polarization resistance (Rpol) 410, which may be relatively large, and may be modeled, for example, as a static value (e.g., 100 mega-Ohms), or as a variable quantity that varies as a function of glucose concentration level.

An estimated analyte concentration level may be determined based upon A) a measured current (charge) flow through the analyte sensor membrane 412 when a voltage is applied to the sensor circuit and B) a glucose sensitivity of the sensor, which correlates a detected current flow to a glucose concentration level.

The change in glucose diffusivity over time presents a problem, in that two unknown variables (glucose concentration around the membrane 412 and glucose diffusivity in the membrane 412) are present in the system. For example, frequent blood glucose meter calibrations may be used to account for the drift, but this need for meter calibrations may be undesirable for a variety of reasons (e.g., inconvenience to the patient, cost, the potential for inaccurate blood glucose meter data, etc.).

With reference to the equivalent circuit 400, when a voltage is applied across the working and reference electrodes 404 and 406, a current may be considered to flow (forward or backward depending on polarity) through the internal electronics of transmitter (represented by R_Tx_internal) 411; through the reference electrode (RE) 406 and working electrode (WE) 404, which may be designed to have a relatively low resistance; and through the sensor membrane 412 (Rmembr, which is relatively small). Depending on the state of the circuit, current may also flow through, or into, the relatively large polarization resistance 410 (which is indicated as a fixed resistance, but may also be a variable resistance that varies with the body's glucose level, where a higher glucose level provides a smaller polarization resistance), or into the double-layer capacitance 408 (i.e., to charge the double-layer membrane capacitor formed at the working electrode 404), or both.

The impedance (or conductance) of the membrane (Rmembr) 412 is related to electrolyte mobility in the membrane, which is in turn related to glucose diffusivity in the membrane. As the impedance goes down (i.e., conductance goes up, as electrolyte mobility in the membrane 412 goes up), the glucose sensitivity goes up (i.e., a higher glucose sensitivity means that a particular glucose concentration will produce a larger signal in the form of more current or charge flow). Impedance, glucose diffusivity, and glucose sensitivity are further described in U.S. Patent Publication No. US2012/0262298, which is incorporated by reference in its entirety.

Determination of Impedance by Measuring Current or Charge Count.

The relationship between impedance (or conductance) of an analyte sensor circuit and analyte diffusivity (e.g., glucose diffusivity) may allow for determination of an accurate glucose sensitivity based upon a determined impedance value of the sensor circuit. In a situation (e.g., in vivo implantation) where the sensor sensitivity is not precisely known, but impedance can be determined from measurements (e.g., using Ohm's law), a predicted sensitivity may be determined based on a correlation between impedance (or conductivity) and glucose sensitivity.

Figure 5A:
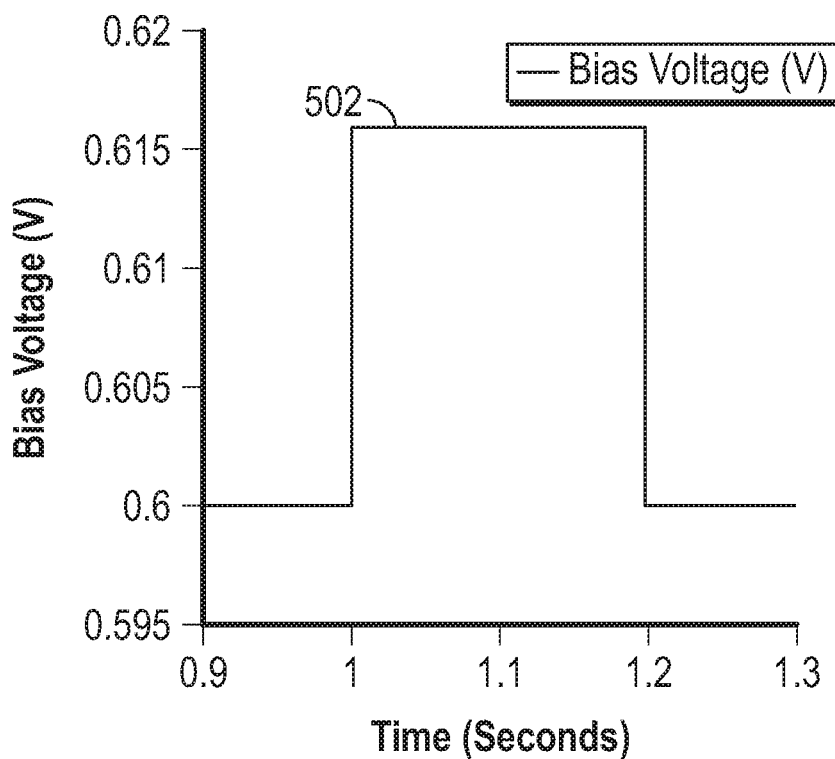
FIG. 5A is a graph that shows a bias voltage step.
Figure 5B:
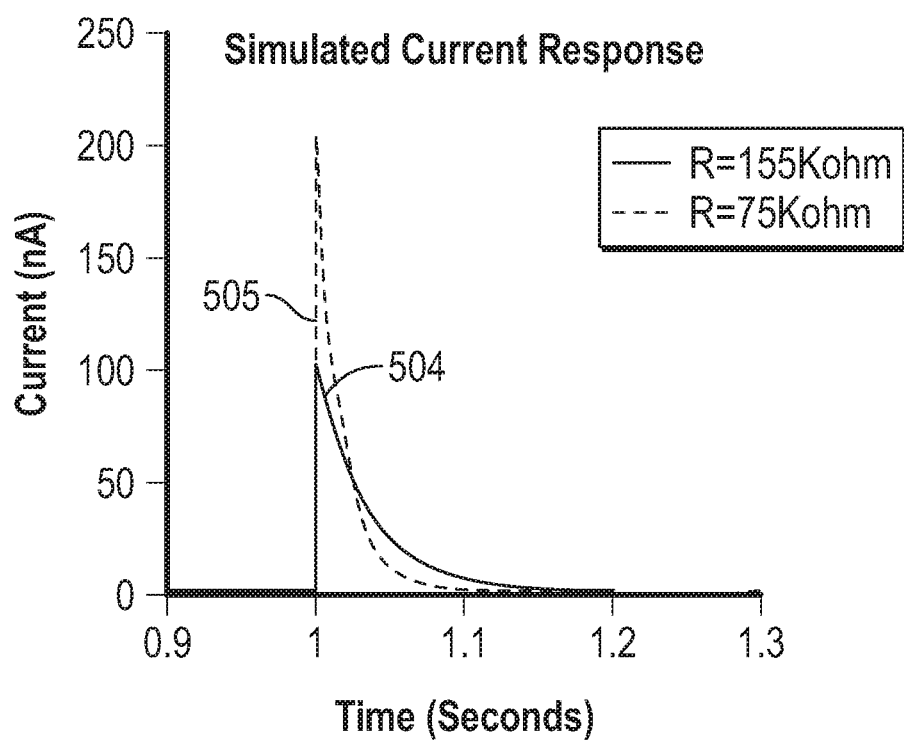
FIG. 5B is a graph that shows a simulated current response to the voltage step shown in FIG. 5A.

In some examples, impedance may be determined based upon application of a known voltage (or voltage step) and measurement of current flow (e.g., integrating charge count over time). In a typical analyte sensor, a sensor bias voltage is applied to a sensor circuit to enable accurate sensing using a sense amplifier. FIG. 5A is a chart that shows a bias voltage 502 stepped up from 0.600 Volts to 0.616 Volts. FIG. 5B shows the corresponding simulated response 504, 505 for a circuit having a 155 kiloohm impedance and a circuit having a 75 kiloohm impedance. As shown in FIG. 5B, the current for the 75 kiloohm circuit rises to a peak current value of over 200 nanoamps, and the response current for the 155 kiloohm circuit rises to about 100 nanoamps. The response current for both circuits then decays as the double-layer capacitance adjusts to the change in applied bias (e.g., as the Cdl in FIG. 4 charges). It should be noted that both FIGS. 5A and 5B illustrate the change in sensor current in response to the transient voltage step. Accordingly, what is shown is the incremental delta current riding on top of an already-existing non-zero glucose current under 0.6V bias.

In a sensor system, a circuit with 155 kiloohm impedance may be differentiated from a circuit with 75 kiloohm impedance based on the magnitude of the current response. In some examples, the impedance may be determined based on the current response, and the resistance attributable to the membrane (Rmembr 412 in FIG. 4) may be determined based upon knowledge (or estimates) of the other impedances in the circuit (e.g., R_TX_internal may be estimated) and Kirchoff's law.

Figure 5C:
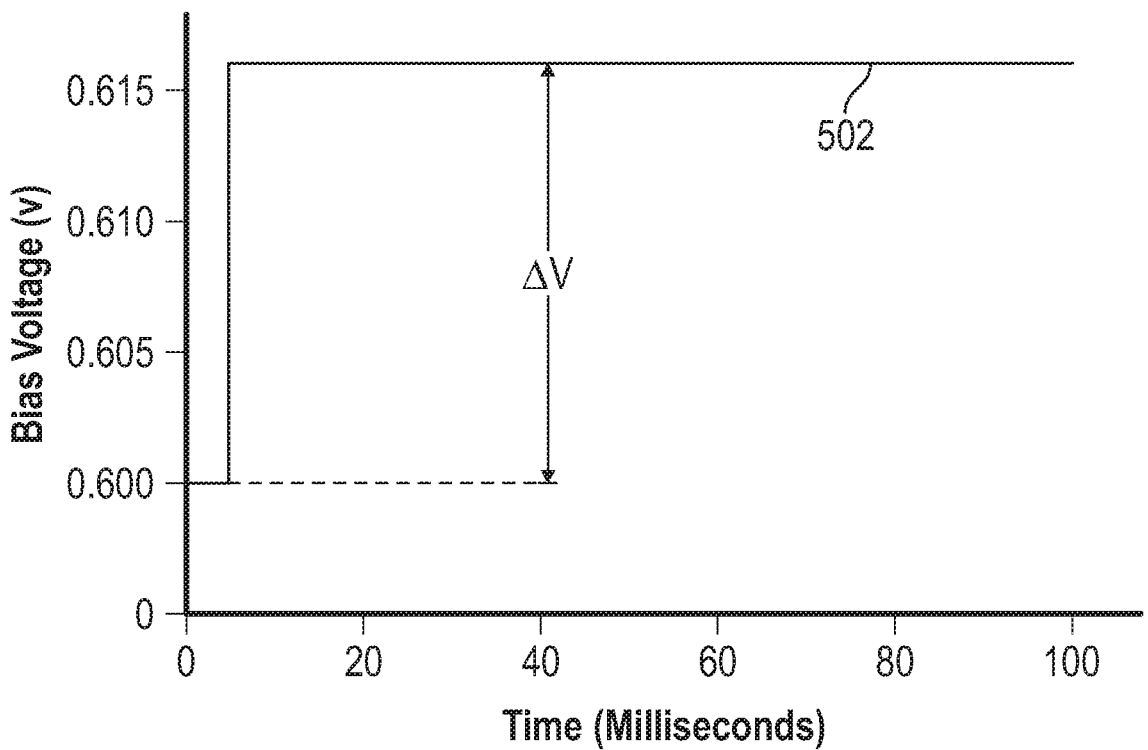
FIG. 5C is a graph that shows the voltage step of FIG. 5A with a time axis in milliseconds.
Figure 5D:
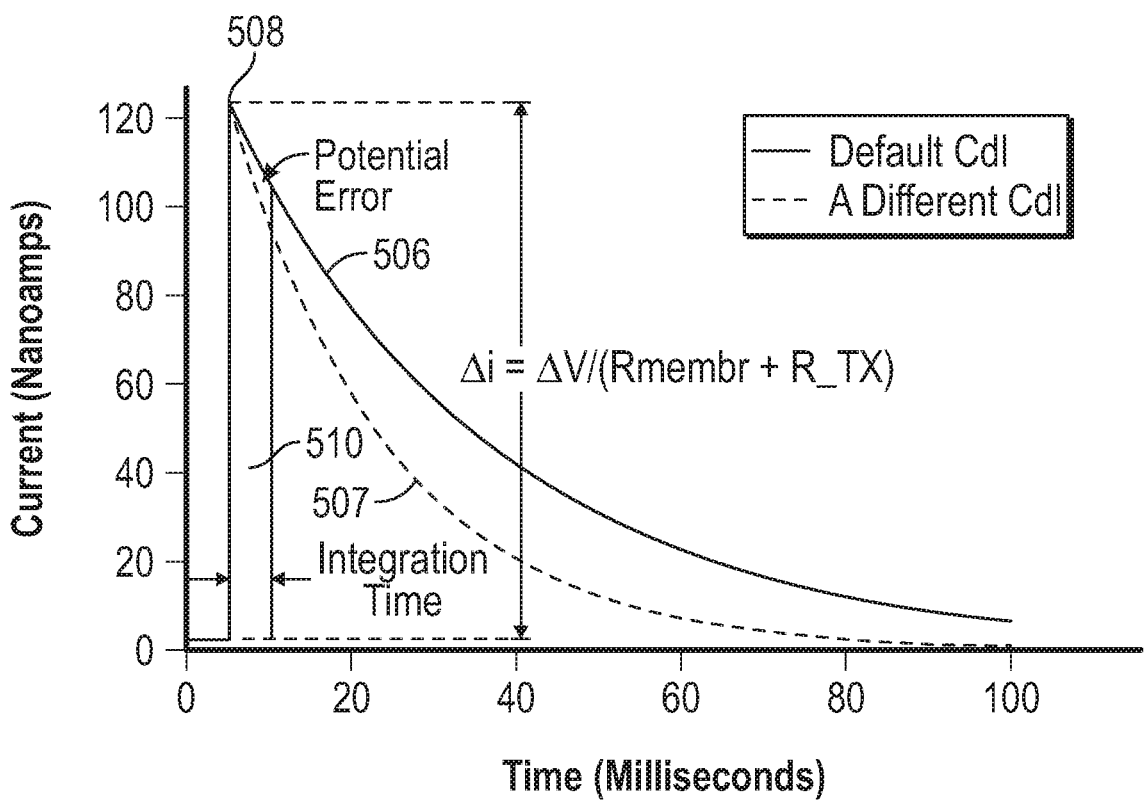
FIG. 5D is a graph that shows the current response to the step of FIG. 5C, with a time axis in milliseconds.

FIG. 5C is a chart that shows a bias voltage 502 stepped up from 0.600 Volts to 0.616 Volts. FIG. 5D shows the current response 506 to the step-up in voltage plotted against time in milliseconds. As shown in FIG. 5D, the sensed current quickly rises to a peak current value 508 (e.g., 120 nA), and then decays as the double-layer capacitance adjusts to the change in applied bias (e.g., as the Cdl 408 in FIG. 4 charges). FIG. 5D also shows a response current 507 for a second sensor with a different double-layer capacitance value, which is described below.

In an analyte sensor, the peak current value 508 may not be measurable directly, but it may be determined by measuring the accumulated charge over an Integration Time 510 (which may, for example, be e.g., 3.9 ms, or a value between 3-5 ms, or a value between 2 and 20 ms, or a value between 2 and 40 ms) after the step-up of the bias voltage, which is the equivalent of integrating under the current response curve for the area A indicated in FIG. 5D.

Simply dividing the integrated current by the specified period of time yields an average current over the integration time, which may be used as an approximation of the peak current, but this approximation is less than the actual peak due to the current decay caused by the double-layer capacitance. A more accurate determination of the peak current may be obtained by assuming a value (e.g., an experimentally determined value) for the double-layer capacitance (Cdl), which allows for derivation of a peak value based upon the integrated current (PI) and the assumed value for Cdl.

Because the capacitance of the membrane (not shown in FIG. 4) may be much smaller than the double-layer capacitance (Cdl), the polarization resistance (Rpol) may be very high (>1 megaOhm), and the capacitive resistance of the membrane is initially very large after the voltage step, substantially all of the current flows through Rmembr 412 and Cdl 408. In a short period (e.g., 5 ms) after the voltage step, the total sensor resistance may be estimated as the membrane resistance (Rmembr 412). The membrane resistance (Rmembr 412) may thus be estimated using Ohm's law: $\Delta i = \Delta V/(Rmembr+R\_TX)$. After the peak current is determined (e.g., based up integrated charge for a short period after the voltage step), this equation may be solved for the resistance of the membrane (Rmembr 412).

An estimate of the integrated pulse current may be obtained by integrating over a small portion of the current decay curve, as shown for example, in FIG. 5D. An integration over a short integration time after the voltage step may be used to estimate peak current. The integration time may be relatively short compared to the time it takes the current response to a step voltage to decay (i.e., compared to the capacitor charge time for the double-layer capacitor after application of the step in bias voltage). For example, an integration time of four milliseconds (4 ms) may be used to estimate peak current. Other important parameters may include the rise time of the voltage step (or bias pulse), the impedance of sensor electronics (which may be measured and consistently controlled in manufacturing), the pulse potential (e.g., a 16 mV step may be applied), and alignment of the current integration with the rising edge of the voltage step (which may be controlled by a clock in the sensor electronics, e.g., the start of the current integration may be one clock cycle after the beginning of a voltage step), and duty cycle (e.g., a five percent duty cycle may be used to allow a sensor membrane capacitance to discharge to a consistent pre-pulse state). In some examples, a voltage step may be applied before each glucose measurement, or recurrently (e.g., before every second glucose measurement, or every third, fourth, or fifth glucose measurement, or once an hour, or once or twice or more times per day).

Figure 5E:
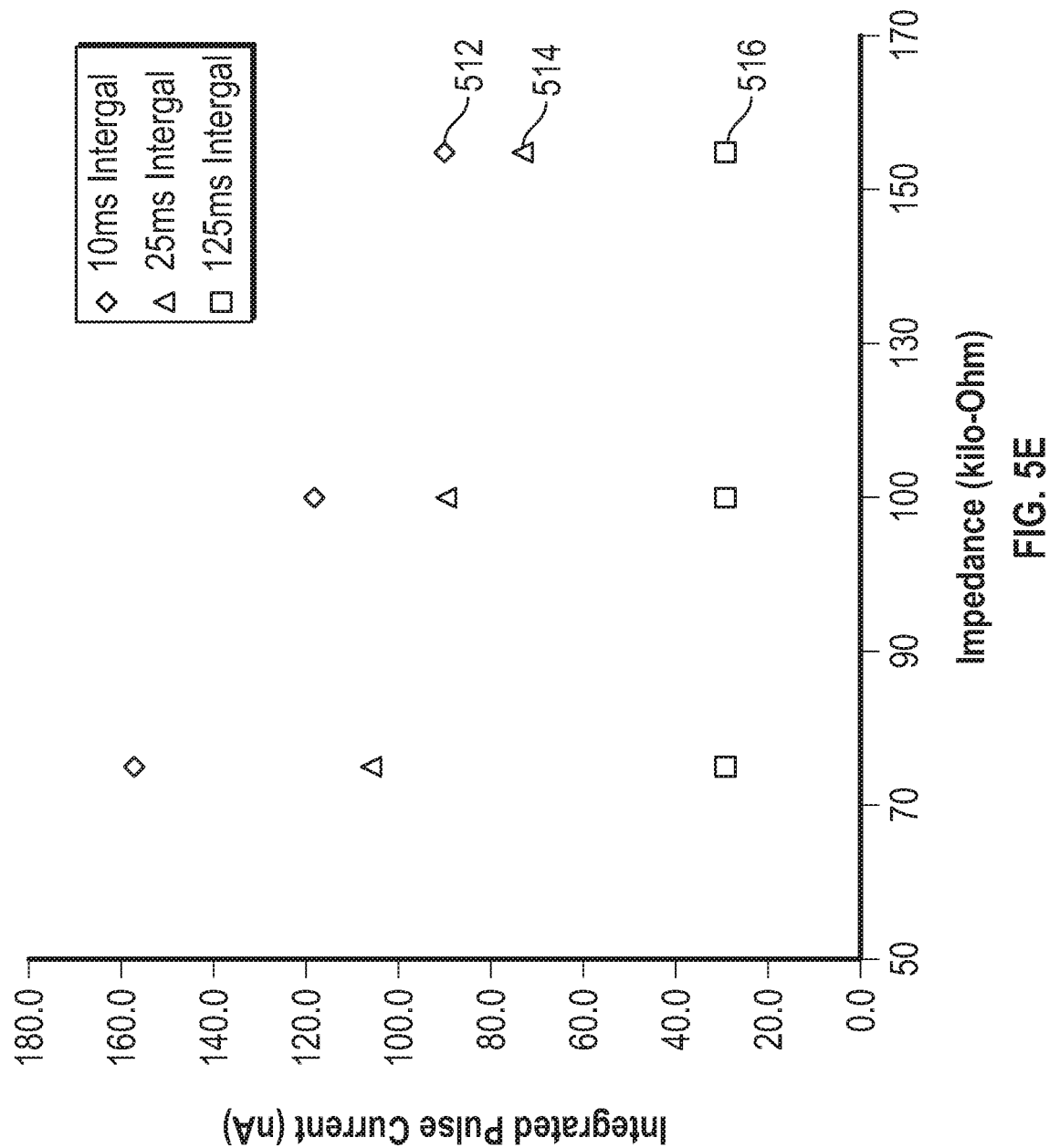
FIG. 5E is a graph that shows integrated pulse current plotted against impedance for three different integration times.

FIG. 5E shows integrated pulse current 512, 514, 516 plotted against impedance for three different integration times (10 milliseconds, 25 milliseconds, and 125 milliseconds). For the 125 millisecond integration time, the integrated pulse current is approximately the same for three different impedance values (75 kOhm, 110 kOhm, 155 kOhm). Because the current is averaged over all or most of the current decay curve (i.e., the current reaches or approaches zero (or a baseline current) within 125 ms), the sensor circuits with different impedances all result in an integrated pulse current of about 30 nanoamps. This approximate equivalence in integrated pulse current for the three different impedance values would prevent determination of an accurate impedance estimate from the integrated pulse currents. In contrast, an integration time of 25 milliseconds results in different values of integrated pulse current for the three different impedance values. As a result, a sensor that integrates over a 25 millisecond integration time would allow for differentiation between sensor circuits having 75 kOhm, 110 kOhm, 155 kOhm impedance values or estimation of an impedance based on integrated pulse current. Using a 10 millisecond integration time provides even greater variation in integrated pulse current for different impedance values, which would improve performance in determining an impedance estimate.

While the description above in some instances discloses absolute current and absolute voltage, it is understood that the methods may also be used with respect to a change in current ($\Delta i$), change in voltage ($\Delta V$), or change in impedance ($\Delta R$). For example, in some analyte sensors, the baseline current may not be zero, because of the presence of a steady bias voltage.

In some examples, a step voltage may be recurrently (e.g., periodically) applied to a sensor circuit. The step voltage may be maintained for a period that is as long or longer than the entire current decay curve, as shown in FIG. 5C, or the step voltage may be returned to a baseline value before the current has decayed to a steady state value, as shown in FIG.

Figure 5F:
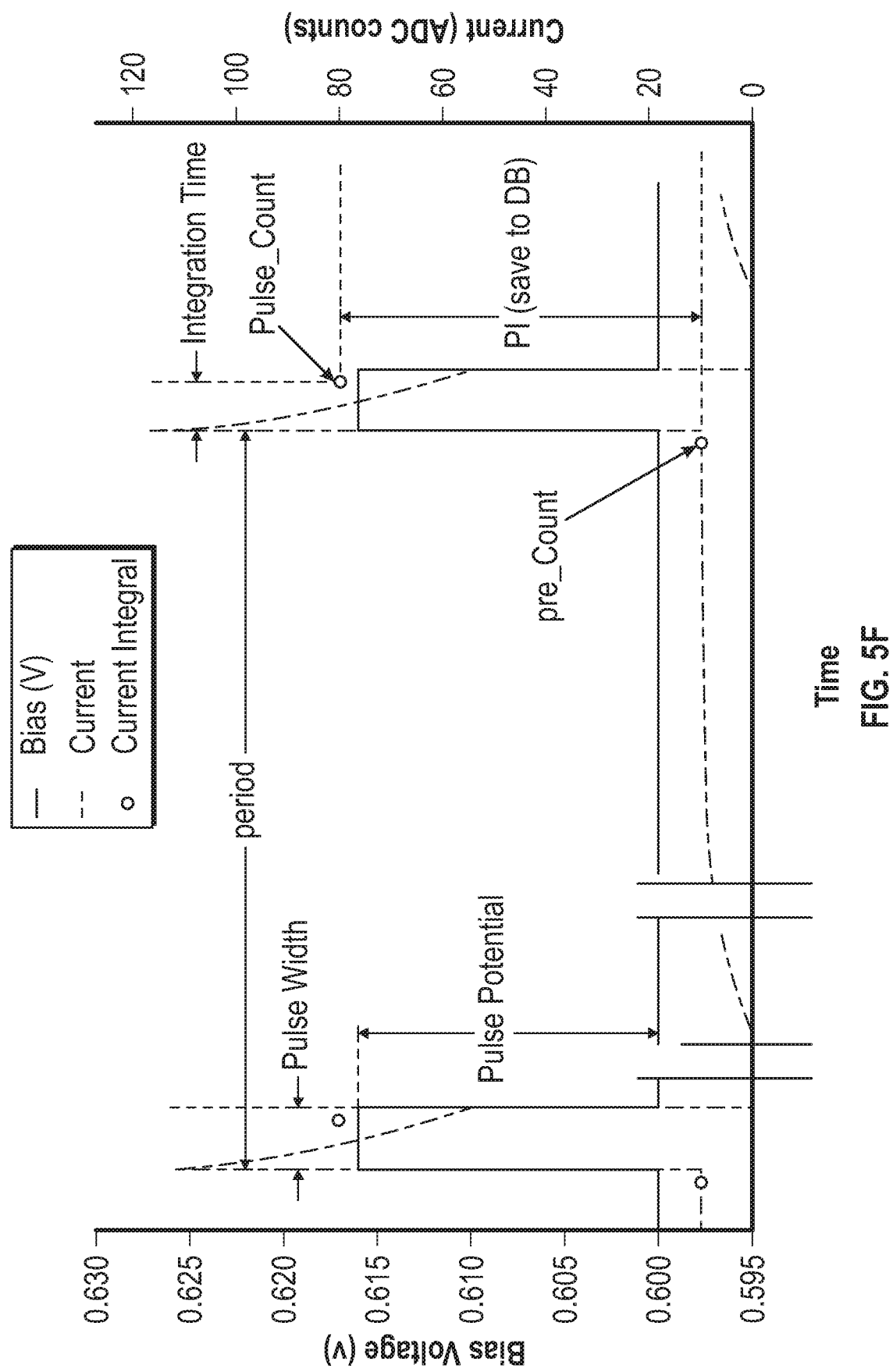
FIG. 5F is a graph that shows bias voltage overlaid onto the current response to a voltage step.

5F. FIG. 5F shows bias voltage overlaid onto the current response to a voltage step ("Pulse Potential"). The step voltage step (e.g., increased from 0.600 Volts to 0.616) may be applied and maintained for a segment of time (Integration Time), and the bias voltage may then be returned to the level it was at prior to the step (e.g., returned to 0.600 Volts). A Current Integral for the Integration Time may be determined based on a difference in a charge count (e.g., obtained using a Coulomb counter) between a count value (Pulse_Count) at the end of the Integration Time and a count value (Pre-_Count) at the beginning of the Integration Time. The Current Integral amounts to an accumulated charge for the pulse (PI), which may be stored in a database (DB) for comparison with past or future impedance values or may be used in a compensation algorithm to provide a more accurate estimated analyte concentration value.

When the bias voltage returns to its normal baseline level (e.g., when the Integration Time period expires and the bias voltage drops from 0.616 Volts back to 0.600 Volts), the capacitor begins to discharge (to move back to a 0.6 Volt charge state), and the observed current drops below the baseline value (because the capacitor is supplying some of the potential to maintain the bias voltage). Eventually, the current transitions back to its baseline (steady state) value.

After a period of time has expired, a second voltage step may be applied, and a second PI value may be determined in the manner described above.

Averaging of Charge Count Values Over Multiple Sampling Periods.

Figure 6A:
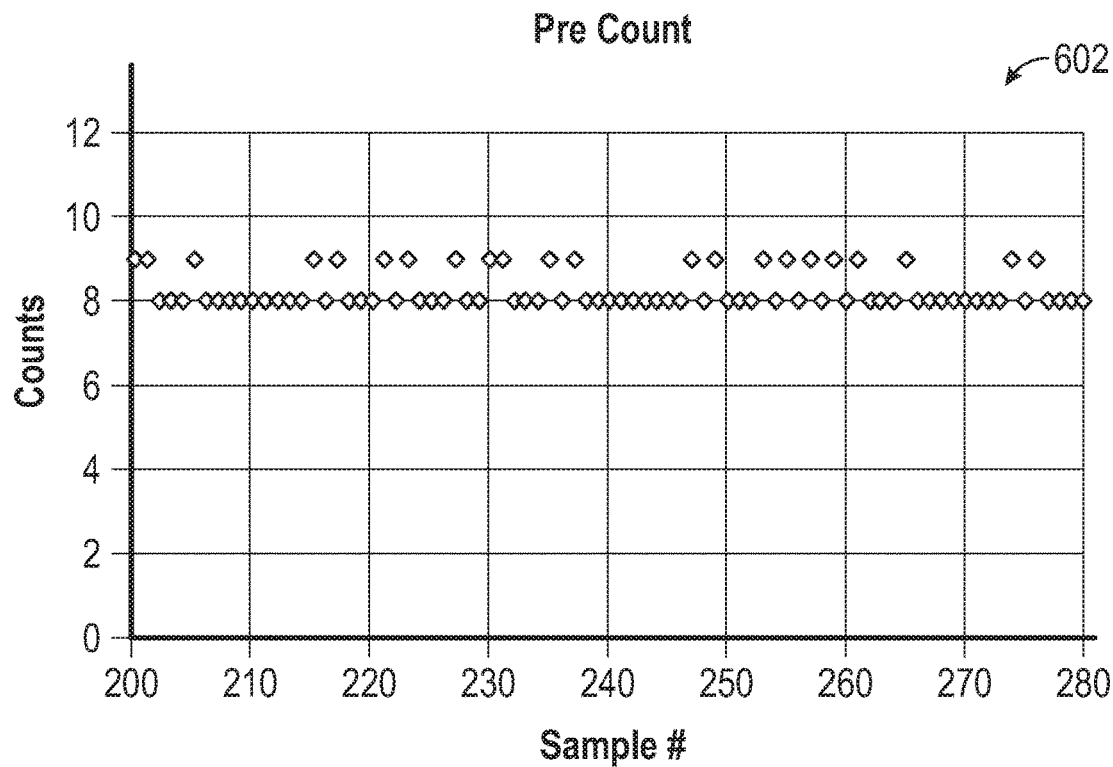
FIG. 6A is a graph that shows count values at the beginning of the Integration Time (Pre_Count) and at the end of the Integration Time (Pulse_Count) for a plurality of samples by a sensor.
Figure 6B:
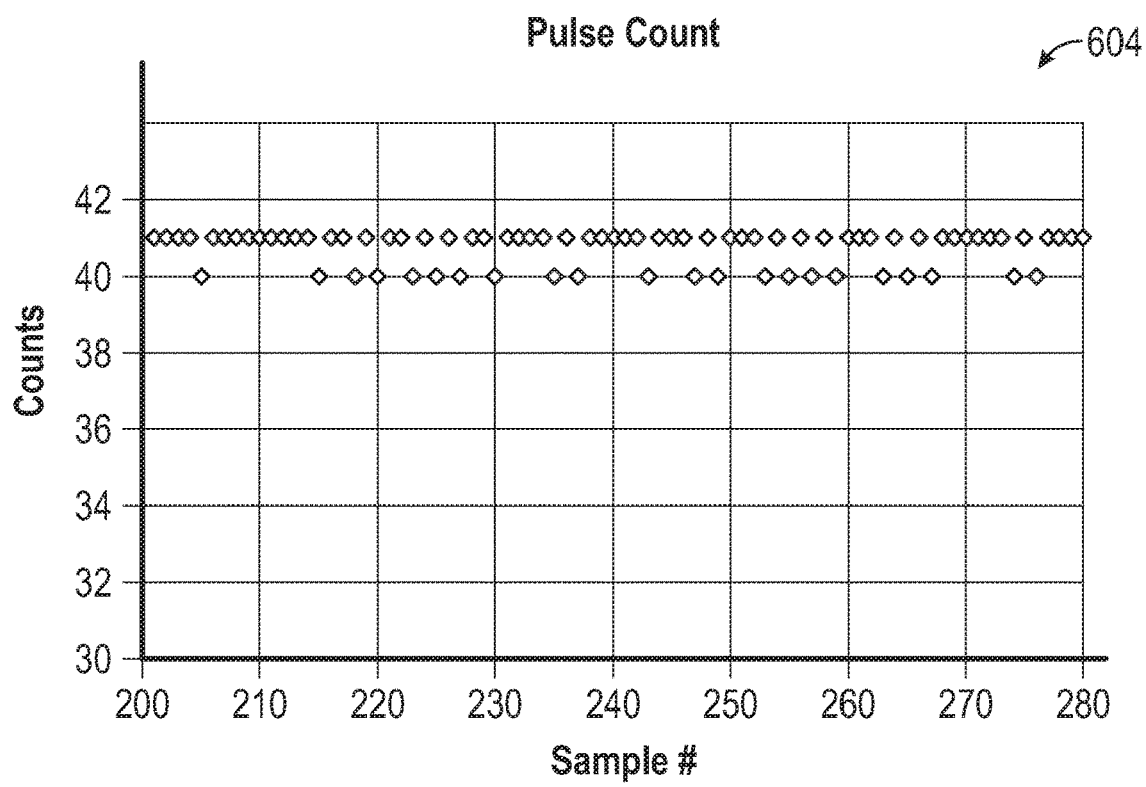
FIG. 6B is a graph that shows count values at the beginning of the Integration Time (Pre_Count) and at the end of the Integration Time (Pulse_Count) for the plurality of sensor samples of FIG. 6A.
Figure 6C:
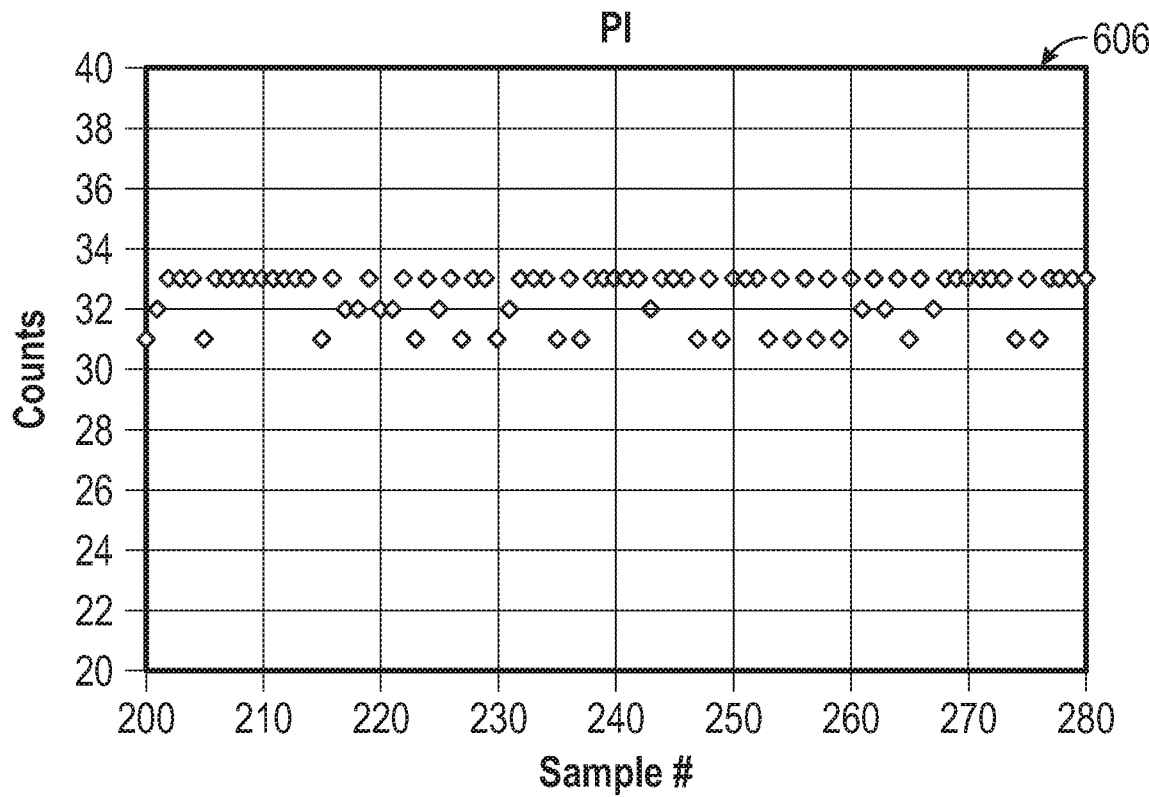
FIG. 6C is a graph that shows integrated charge count (PI) for the samples of FIGS. 6A and 6B.
Figure 6D:
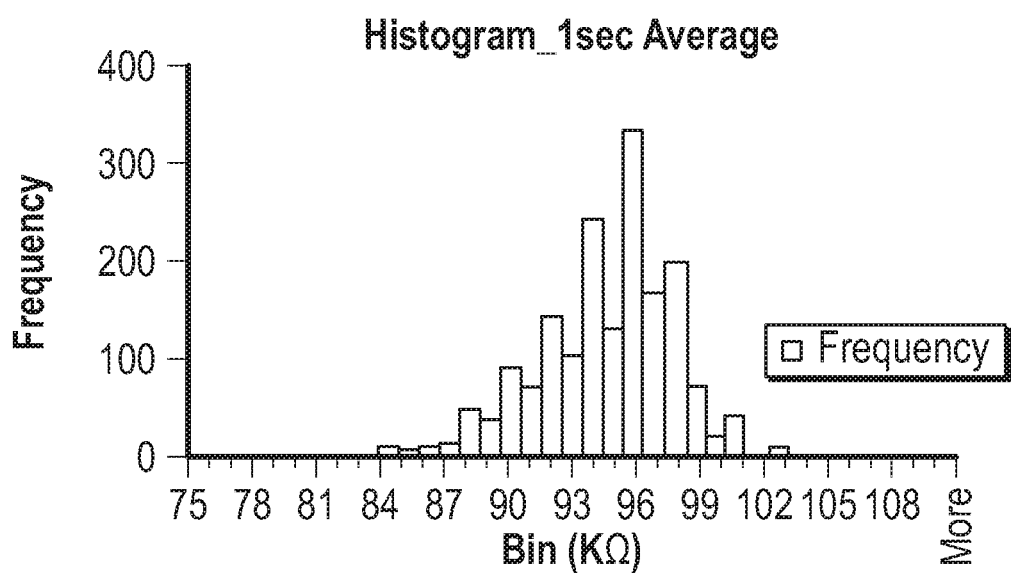
FIG. 6D is a histogram plot of determined impedance for a sensor, where charge count was averaged over a plurality of one-second sampling periods.
Figure 6E:
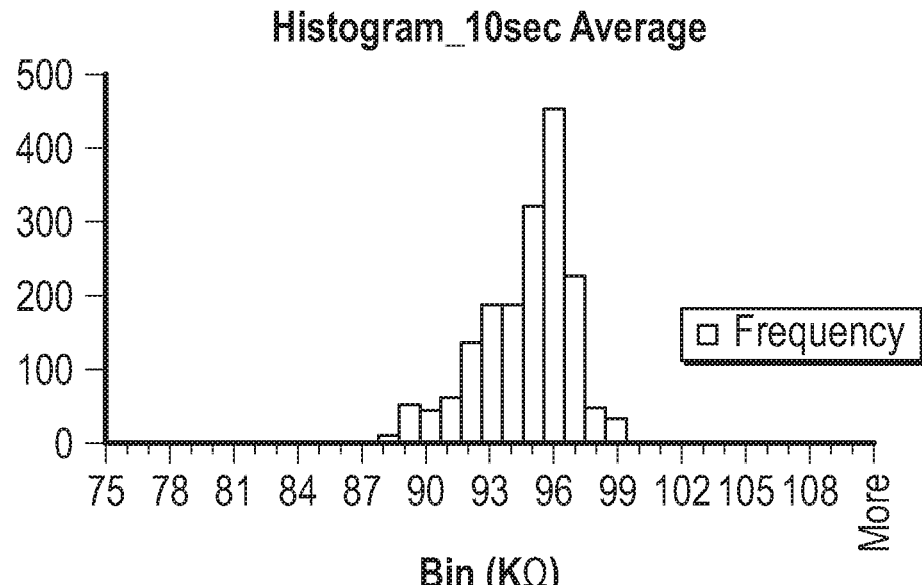
FIG. 6E is a histogram plot of determined impedance for a plurality of ten-second sampling periods.
Figure 6F:
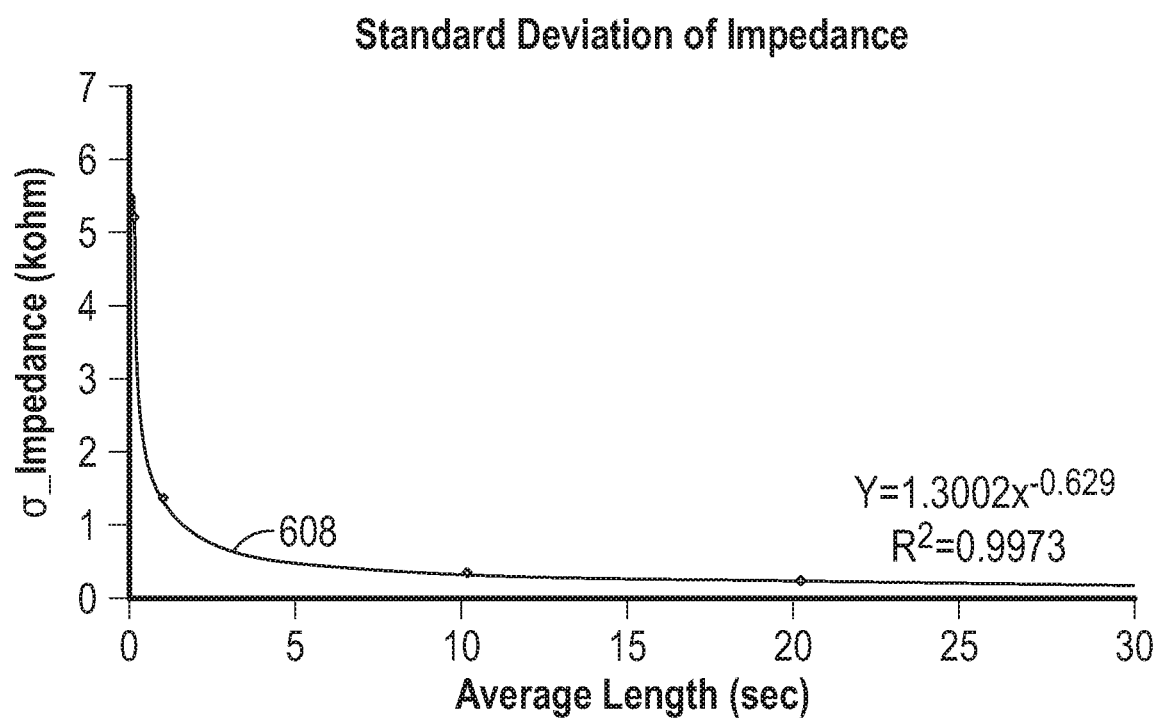
FIG. 6F is a graph that shows the standard deviation of determined impedance values for a sensor plotted against a length of time over which current (e.g., integrated charge count) was measured or determined.

FIGS. 6A and 6B show respective count values 602, 604 at the beginning of the Integration Time (Pre_Count) and at the end of the Integration Time (Pulse_Count) for a plurality of samples by a sensor. FIG. 6C shows the integrated charge count (PI) 606 for the Integration Time (Pulse_Count-Pre_Count.) The counts for multiple Integration Times in a sampling interval (e.g., 1 second, 10 seconds, 12 seconds, or 20 seconds) maybe be averaged to determine an average (e.g., mean or median) integrated charge count (PI), which may increase the accuracy of the charge count (PI) or increase the accuracy of an impedance or sensitivity derived therefrom. FIG. 6D shows a histogram plot of determined impedance for a sensor, where charge count was averaged over a plurality of one-second sampling periods (e.g., at a rate of one sample every 5 milliseconds during the sampling period). FIG. 6E is a histogram plot of determined impedance for a plurality of ten-second sampling periods. The histogram based on ten-second sampling periods provides a tighter distribution (e.g., more clustering around 96 kΩ and a tighter standard deviation). While using an average value from a plurality of Integration Times may improve the accuracy of the integrated charge count (PI) and impedance or sensitivity derived therefrom, obtaining a large data set may have an adverse impact on battery life due to energy consumed in applying the voltage step and processing the resulting current. FIG. 6F shows the standard deviation of determined impedance values 608 for a sensor plotted against a length of time over which current (e.g., integrated charge count) was measured or determined. In some examples, an averaging time of about 1 second (e.g., 0.5 to 1.5 seconds, or 0.5 to 3 seconds) is used, to provide a set of determined impedance values having a standard deviation of less than 2 Ohms. In some examples, an averaging time of about 10 seconds or 12 seconds (e.g., 5 to 15 seconds, or 8 to 12 seconds, or 10 to 14 seconds) is used to collect current (e.g., integrated charge count) values, which may provide a set of determined impedance values with a standard deviation of less than 1 Ohm.

The Relationship Between Impedance and Sensitivity.

Figure 7A:
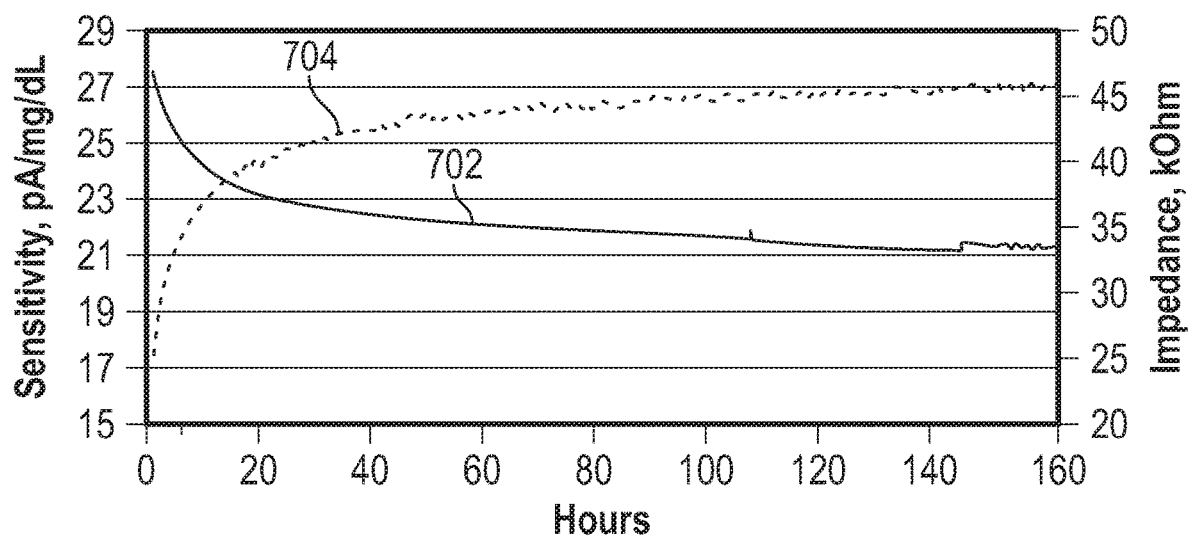
FIG. 7A is a graph that shows experimental data plotted against time, where impedance was measured from a tested sensor, and sensitivity was determined by placing the tested sensor in a solution having a known glucose concentration (e.g., a known mg/dL of glucose) and measuring a current.
Figure 7B:
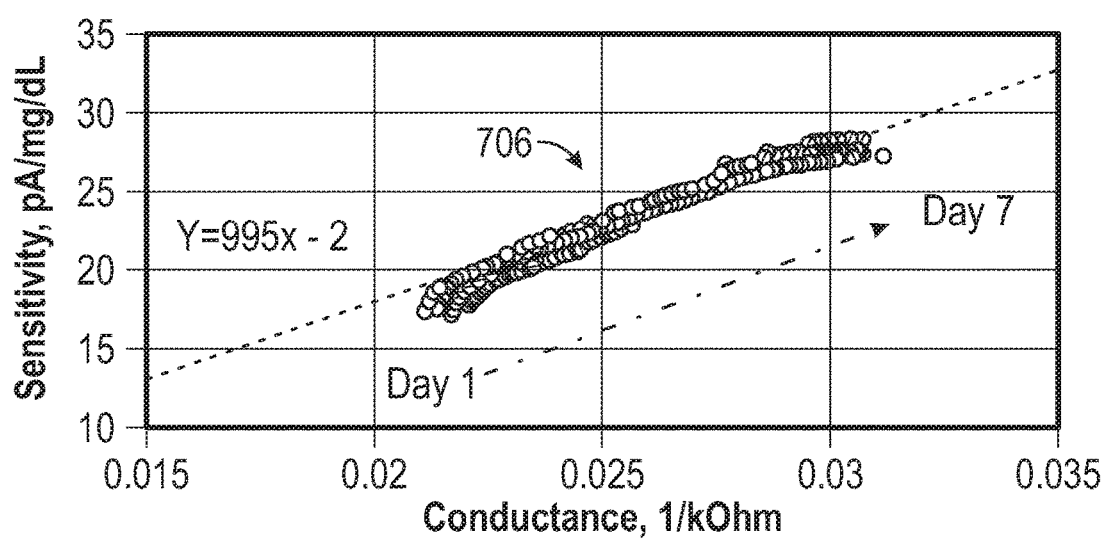
FIG. 7B is a graph that shows sensitivity plotted against conductance.

A correlation has been observed between the estimated impedance (e.g., resistance in a DC circuit) and the glucose sensitivity of a sensor. FIG. 7A shows experimental data plotted against time, where impedance 702 was measured from a tested sensor, and sensitivity 704 was determined by placing the tested sensor in a solution having a known glucose concentration (e.g., a known mg/dL of glucose) and measuring a current (e.g., in pA) in the tested sensor circuit (e.g., using sensor electronics). As can be seen from the graph, impedance 702 falls over time and glucose sensitivity 704 rises. FIG. 7B shows sensitivity 706 plotted against conductance (which is the inverse of impedance) for a number of sensors. A linear relationship between sensitivity and conductance (e.g., y=995x−2, or Sensitivity=995(Conductance)−2) may be observed from the data in FIG. 7B. The relationship between sensitivity and conductance may be used to determine a sensitivity in a sensor (e.g., an implanted sensor) having an unknown sensitivity and a conductance determined from a sensor measurement (e.g., the inverse of a measured impedance as described above). In some examples a functional range of the relationship may be defined. For example, a function range may be defined as in which the relationship between conductance and sensitivity is linear or approximately linear, such as 0.023 to 0.030 in FIG. 7B.

Double-Layer Capacitance Mitigation

While an impedance may be determined by assuming a default value for double-layer capacitance, such an assumption may introduce an error due to a difference between an actual double-layer capacitance and the assumed default capacitance. In some examples, the assumed default capacitance is the capacitance of a text unit for calibrating an analyte sensor transmitter on the bench.

In reference to FIG. 5D, the current response 506 may represent an assumed (e.g., default) double-layer capacitance (Cdl), which has a first current decay rate. As the capacitor charges, the current flow falls off. The second current response 507 shown in FIG. 5D may represent an actual current response of a particular sensor that has a double-layer capacitance that is smaller than the assumed double-layer capacitance. The observed current response 507 decays more quickly than current response 506, due to the smaller capacitance of the sensor associated with current response 507. As a result, the integrated charge during the Integration Time will be lower (i.e., the area under the curve is smaller) for current response 507 of the sensor than for a sensor having the assumed capacitance that produces the current response 506. When sensor electronics determine an impedance for a sensor that has current response 507, but the computations assume the current response 506, the resulting determined impedance will include an error, i.e., the inferred peak will be lower than it actually is, and the determined impedance (based on the erroneously low peak current value) will be higher than it would be if the true double-layer impedance and resulting current response 507 were used in the determination. In other words, failing to account for the actual double layer capacitance (Cdl), which varies from sensor to sensor, will result in inaccurate estimates of the membrane resistance (Rmembr.)

Figure 8A:
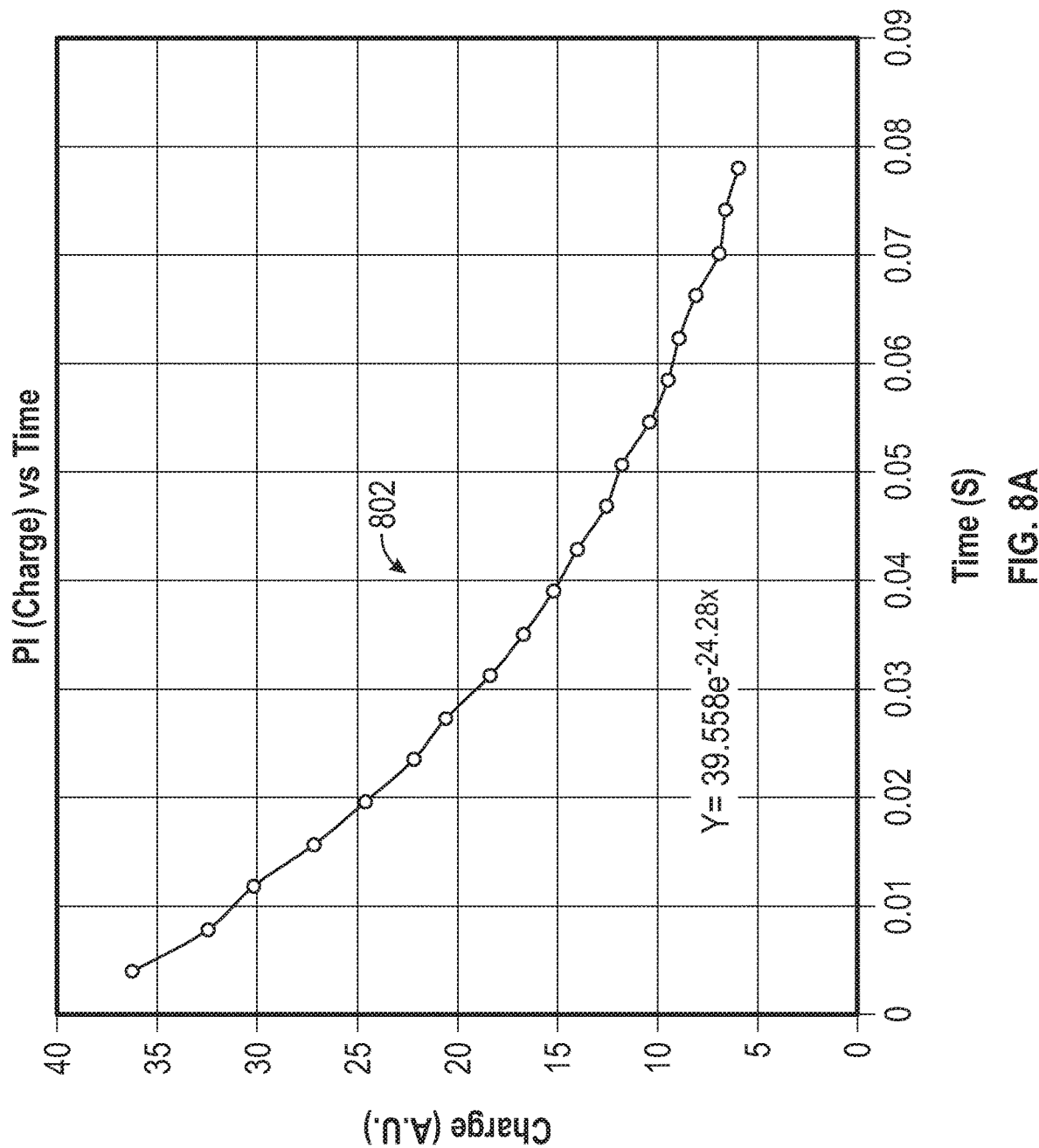
FIG. 8A is a graph that shows integrated charge for a number of sequential time periods.

In some examples, the current response 506 may be estimated by repeated integrations of charge (current) over a number of Integration Time periods during the current decay. For example, charge may be integrated over sequential Integration Time periods to construct a decay curve. FIG. 8A shows an example in which integrated charge 802 for a number of sequential Integration Time periods (e.g., 3.9 ms) is plotted against time to produce a decay curve. Theoretically, the current response i(t) is described by the equation: $i(t)=(Vstep)/Rmembr*e^{(-t/Rcoat*Cdl)}$. By fitting the curve to an exponential trend (e.g., $y=39.558e^{-24.28x}$), the 1/Rmembr*Cdl factor can be extracted (e.g., 1/Rmembr*Cdl=1/24.8=40 ms in the illustrated example). The current level at the time at which the step was applied (i.e., time zero) may not be known from measurement, as the integration takes a period of time (e.g., 3.9 ms), so the measured current flow for the first period represents an average over the first period. The current value at time zero may be determined as the factor in front of the exponential in the fitted equation (curve). For example, in the equation above, the current flow at time zero is 39.558, which represents the intercept obtained by extrapolating the curve back to the zero seconds point (T=0) on the curve. By reconstructing the current response curve, the intercept at t=0 can be estimated, yielding a more accurate value for Rmembrane.

FIG. 8B shows two current response curves 820, 830 with the same peak (35 nanoAmps) but a different decay rate. The first curve 820 may represent a sensor at a first time after implantation in a host, and the second curve 830 may represent the same sensor at a second time. For example, the sensor may have a membrane resistance (Rmembr) of 50 kiloOhms, the first curve 820 may reflect a double layer capacitance of 100 nanoFarads, and the second curve 830 may represent a double layer capacitance of 200 nanoFarads. The intercept at time zero (t=0) is the same.

FIG. 8C shows integrated charge for a plurality of sequential equivalent Integral Time periods for the first curve 820' and the second curve 830' (which means that the Sample Number axis is in effect a time axis). As can be seen from FIG. 8C, if an integral is taken only for the first Interval Time period (e.g., with reference to FIG. 8B, charge or current integrated to point 821 on the first curve 820 and integrated to point 831 on the second curve 830), the resulting integrated charge 832 for curve 830' is larger than the resulting integrated charge 822 for curve 820' because curve 820' has a higher decay rate as a result of a lower double-layer capacitance of the sensor membrane. If impedance is determined from the integrated charge or measured current (e.g., if the capacitance and decay rates are ignored), this difference in integrated charge (or current) would result in a difference in determined impedance. Sensitivities determined based on the impedances determined from the two curves would also be different, reflecting the error caused by capacitance.

In contrast, sampling more points and fitting an exponential trendline (as described above) produces the same estimated intercept (or approximately the same and much more accurate than a single integral) at t=0 e.g., 3e−10 C) for both curves. From this value, the membrane resistance (Rmembr) may be calculated as: Rmembr=integration time*(Vstep/integrated charge)=0.001*0.015/3e−10=50 kOhm.

FIG. 8D shows integrated charge values 822', 832' plotted on a logarithmic scale against sample number (which correlates with time because the samples are taken at regular intervals), which produces a linear relationship between current (or charge) and the sample number.

Another example method of correcting for differences in double-layer capacitance between an assumed default capacitance and the double-layer capacitance of a sensor is illustrated by the following equation:

$$\hat{R}_M = -\frac{\Delta t}{C_{dl} \times \ln\left(1 - \frac{PI}{\overline{V} \times C_{dl}}\right)}$$

In the above equation, PI is the integration of a pulse current recorded by a transmitter or other sensor electronics associated with a sensor. $\overline{V}$ is a transient excursion bias voltage. For example, referring again to FIG. 5A, the transient excursion bias voltage in the illustrated example is 16 mV (e.g., a pulse from 600 mV to 616 mV). $C_{dl}$ is the double-layer capacitance of the membrane. $\Delta t$ is the duration of the integration of the current from the sensor. The relationships indicated by the equation above can be used to determine the membrane impedance for a sensor or a combination of a sensor and sensor electronics in circumstances in which the double-layer capacitance is known. In some examples, the relationships indicated by the equation above can also be used to characterize the membrane impedance in an in vivo sensor in which both membrane impedance and double-layer capacitance are unknown. For example, the sensor electronics can apply multiple transient bias pulses and measure the integrated pulse current (PI) over each of the transient pulses. Data from multiple pulses and multiple integrations can be used to solve for membrane impedance in an in vivo scenario where double-layer capacitance is also unknown.

Figure 9:
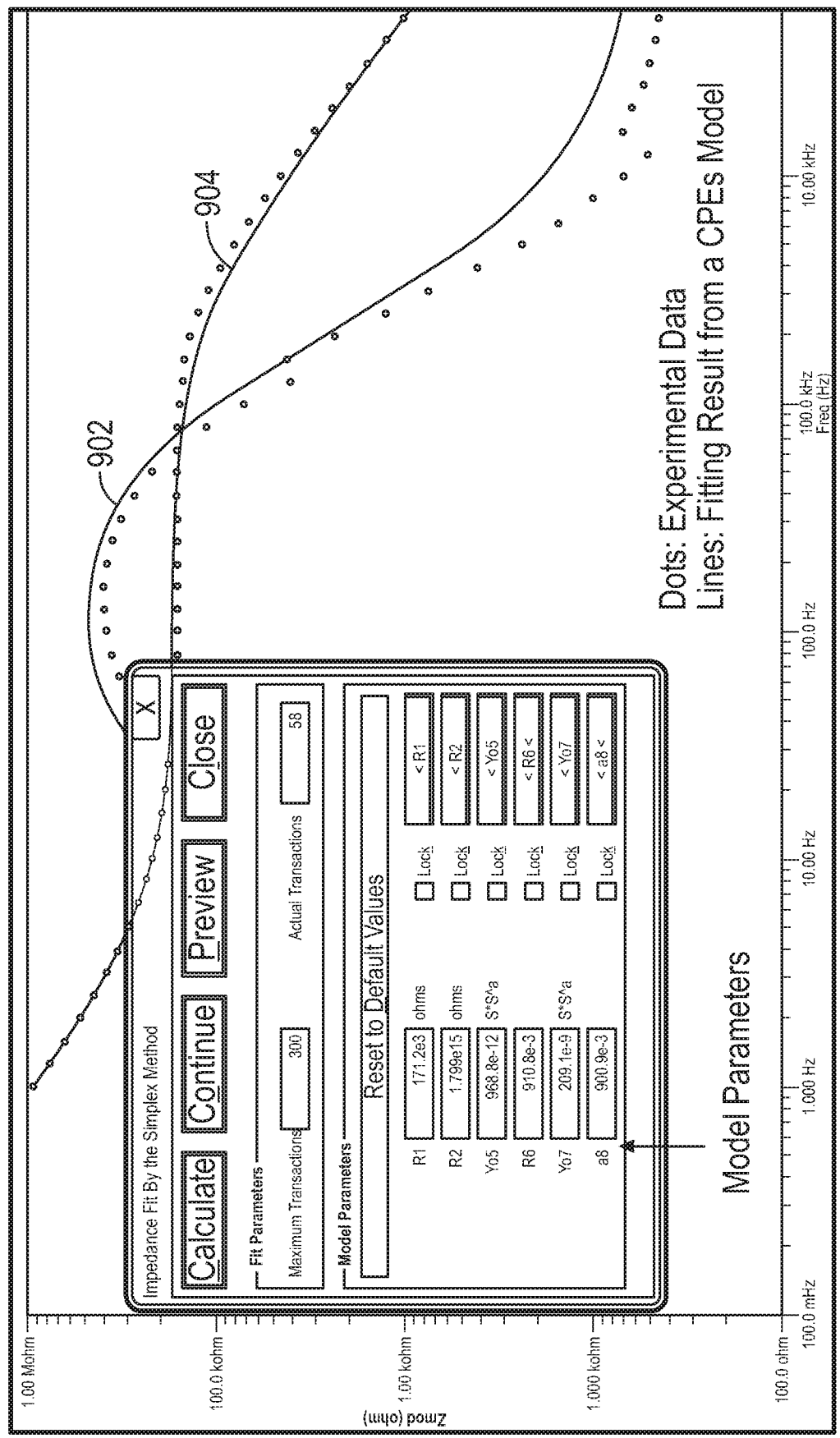
FIG. 9 shows an example curve-fitting for impedance and frequency data.

In some examples, a curve-fitting technique may be applied to an impedance spectroscopy data set (e.g., impedance at a plurality of frequencies). FIG. 9 shows an example curve-fitting, where dots indicate data from sensor testing (e.g., determined impedance values at various frequencies) and lines 902, 904 indicate fitted model for the sensor data. Software and a model may be used to determine a fit for the measured sensor data.

Figure 10:
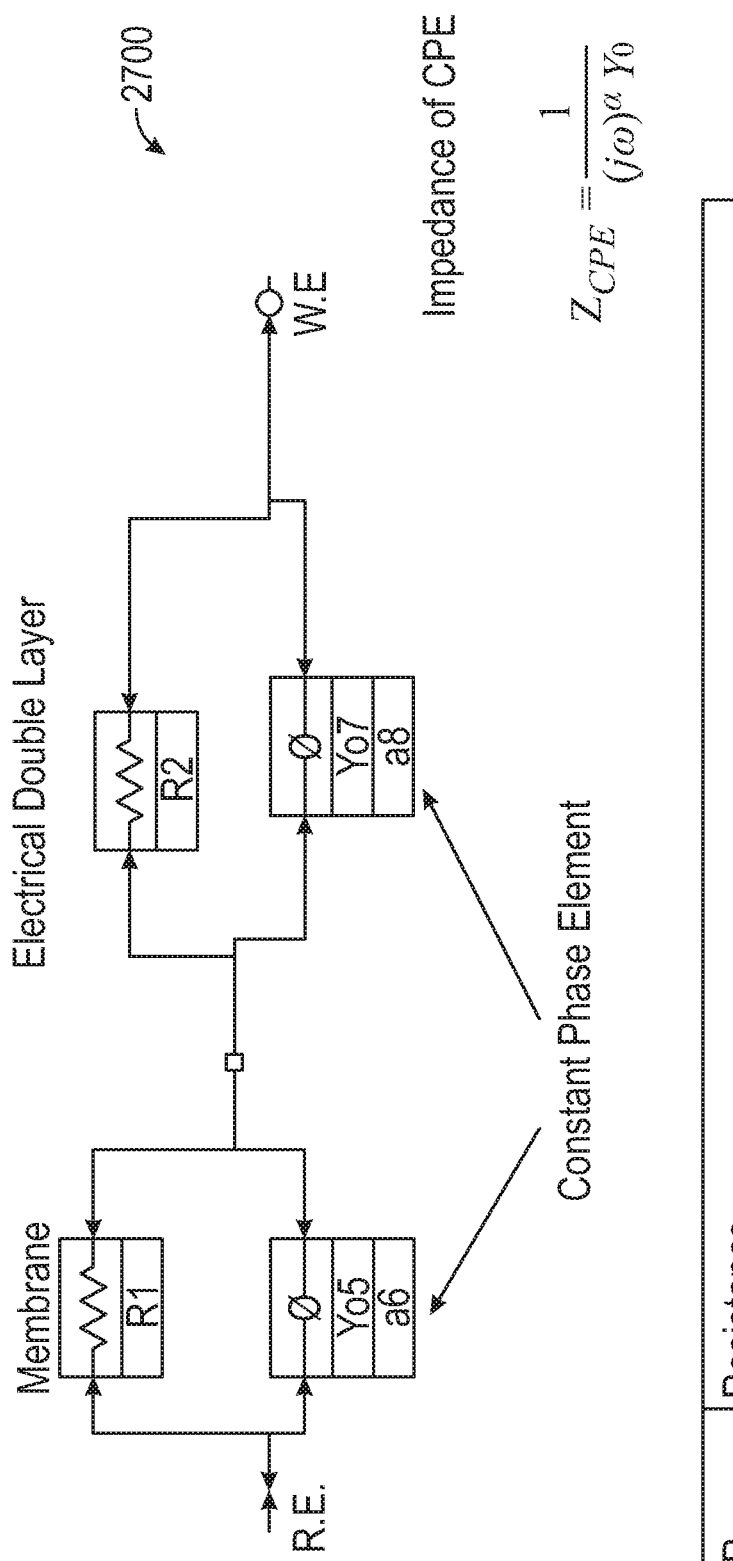
FIG. 10 is a schematic illustration of a constant-phase element (CPE) model.

In some examples, a constant-phase element model may be used to fit impedance spectroscopy data. A capacitor in an electrochemical sensor system may not behave ideally. For example, the double-layer capacitor (described above) formed by a membrane of an analyte sensor may behave according to a constant-phase element model, as opposed to a capacitor. FIG. 10 is a schematic illustration of a constant-phase element (CPE) model 1000, where R is resistance, Yo is a "pseudo" capacitance, and alpha is an exponent that equals 1 for a capacitor. A sensor may be tested to determine impedance across a range of frequencies, a fit may be determined (e.g., using a model), and the sensor may be declared healthy if one or more or a combination of the fitted parameters satisfies one or more health conditions. For example, the tested sensor may be declared healthy based upon a comparison of one or more parameter values to one or more respective thresholds. In some examples, a slightly damaged sensor may be identified based on a condition, and either approved for use, or compensated based on a measure of potential damage such as one or more of the model parameters.

Eight sensors were fitting using the CPE model explained above, where two sensors (denoted A and B) were healthy (undamaged), two sensors (denoted C and D) were badly damaged, and four sensors (E, F, G, and H) were slightly damaged.

Figure 11A:
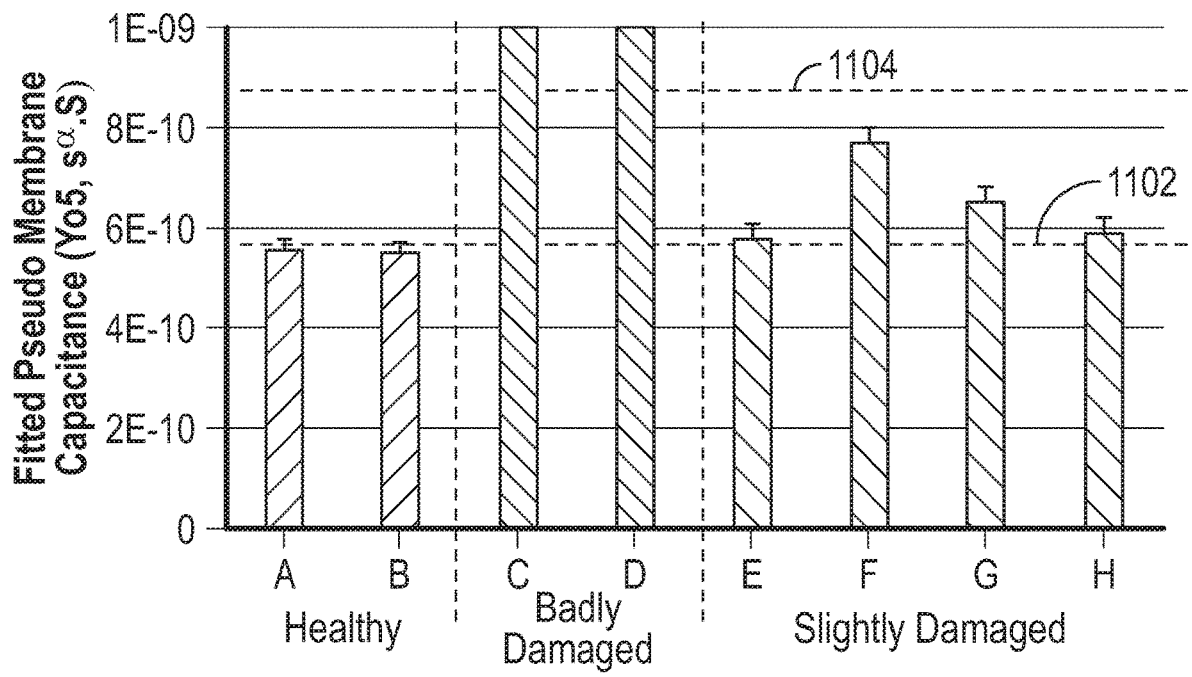
FIG. 11A is a chart that shows fitted pseudo membrane capacitance, determined using a CPE model, for eight sensors.

FIG. 11A shows fitted pseudo membrane capacitance for each of eight sensors, determined using the CPE model described above. The healthy sensors (sensors A and B) have the lowest fitted pseudo membrane capacitance in the group, the heavily damaged sensors (C and D) have the highest fitted pseudo membrane capacitance, and the slightly damaged sensors (E-H) have fitted pseudo membrane capacitance values between values for the healthy sensors and the badly damaged sensors, which indicates that the fitted pseudo membrane capacitance may be used to distinguish healthy sensors from damaged sensors. For example, a sensor may be tested, and a sensor status may be determined based on the fitted pseudo membrane capacitance relative to one or more thresholds, which may be determined from a population of tested sensors with known damage states (e.g., determined from a microscope inspection or protocol for inflicting damage, or both). In an example, a sensor may be declared healthy if the fitted pseudo membrane capacitance is below a first threshold 1102, a sensor may be declared badly damaged responsive to the fitted pseudo membrane capacitance being above a second threshold 1104, and a sensor may be declared slightly damaged (e.g., in need of appropriate compensation) if the fitted pseudo membrane capacitance is between the first and second thresholds 1102, 1104. In various examples, more or fewer threshold may be used, and a threshold may additionally or alternatively be applied to one or more of the other parameters represented in FIGS. 11A-E. In some examples, a probability of sensor damage may be determined based on one or more parameter values. In some examples, an estimate of an extent of sensor damage, or an amount of compensation, may be determined based on one or more parameters values. Such a probability or estimate may be used to determine whether to use a sensor (e.g., designate a sensor for removal from a production process, or indicate to a user to replace the sensor), or whether to apply compensation.

Figure 11B:
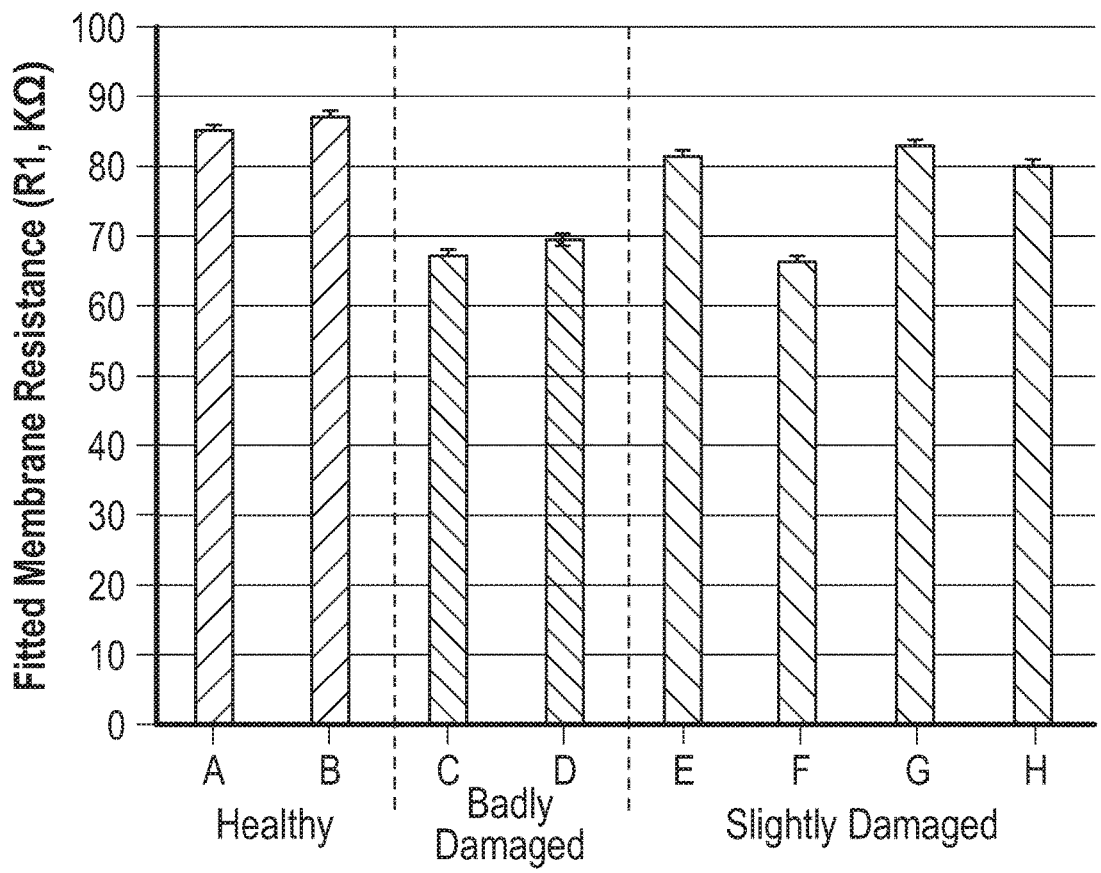
FIG. 11B is a chart that shows fitted membrane resistance for each of the eight sensors (also determined using the CPE model described above.)

FIG. 11B shows fitted membrane resistance for each of the eight sensors (also determined using the CPE model described above). The healthy sensors (sensors A and B) have a fitted membrane resistance that is significantly higher than the fitted membrane resistance of the heavily damaged sensors (C and D). The slightly damaged sensors (E, F, G, H) have an average fitted membrane resistance value that is between the values for the healthy sensors and the values for the badly damaged sensors. These relationships in fitted membrane resistance indicate that the fitted membrane resistance may be used to distinguish healthy sensors from damaged sensors. For example, a sensor may be tested to determine impedance across a range of frequencies, a fit may be determined (e.g., using a model), and the sensor may be declared healthy if the fitted membrane resistance satisfies a health condition. For example, the tested sensor may be declared healthy responsive to the fitted membrane resistance exceeding 82 kiloohms. In some examples, a slightly damaged sensor may be identified based on a fitted membrane resistance condition (e.g., R1 between two thresholds), and slightly damaged sensor may be approved for use or compensated (e.g., compensated based on a measure of potential damage, such as the fitted membrane resistance value, or another model parameter, or combination or parameters).

Figure 11C:
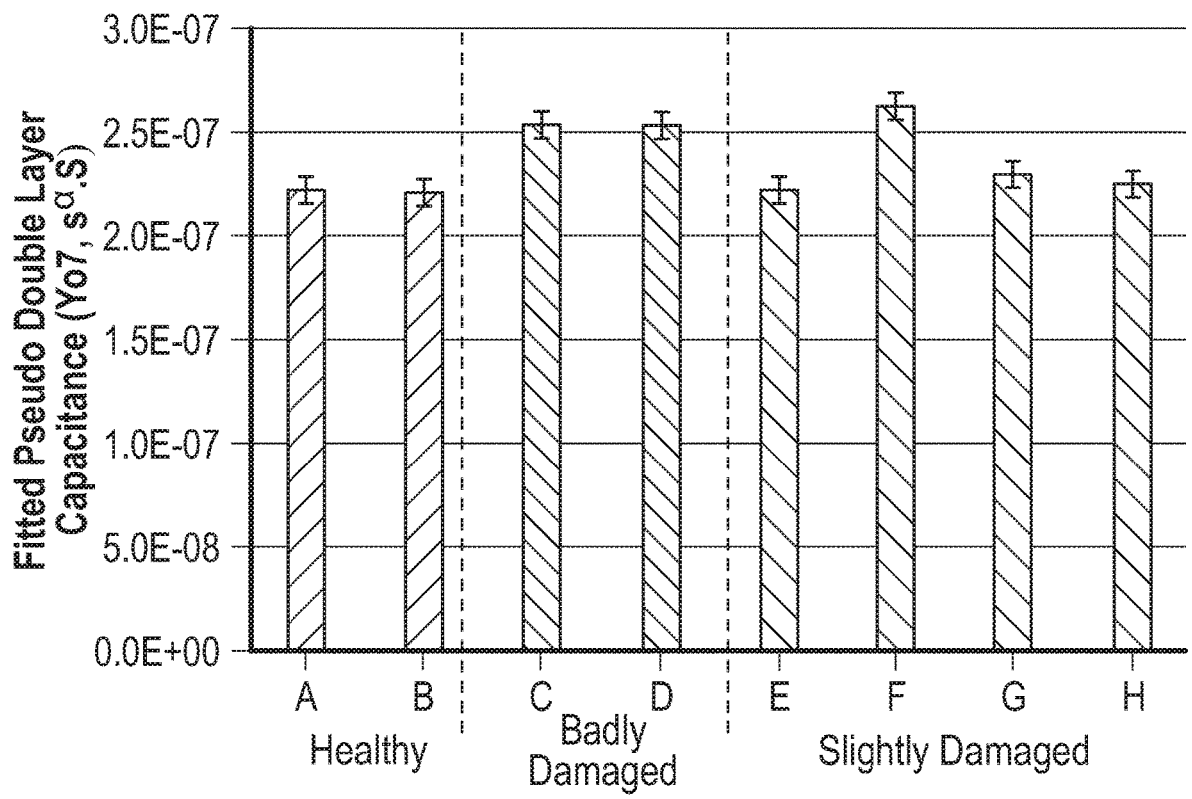
FIG. 11C is a chart that shows fitted pseudo double layer capacitance for the eight sensors.

FIG. 11C shows fitted pseudo double layer capacitance for the eight sensors. The healthy sensors (sensors A and B) have a fitted pseudo double layer capacitance that is lower than fitted pseudo double layer capacitance of the heavily damaged sensors (C and D). The slightly damaged sensors have fitted pseudo double layer capacitance values that are between the values for the healthy sensors and the values badly damaged sensors, which indicates that the fitted pseudo double layer capacitance may be used to distinguish healthy sensors from damaged sensors.

Figure 11D:
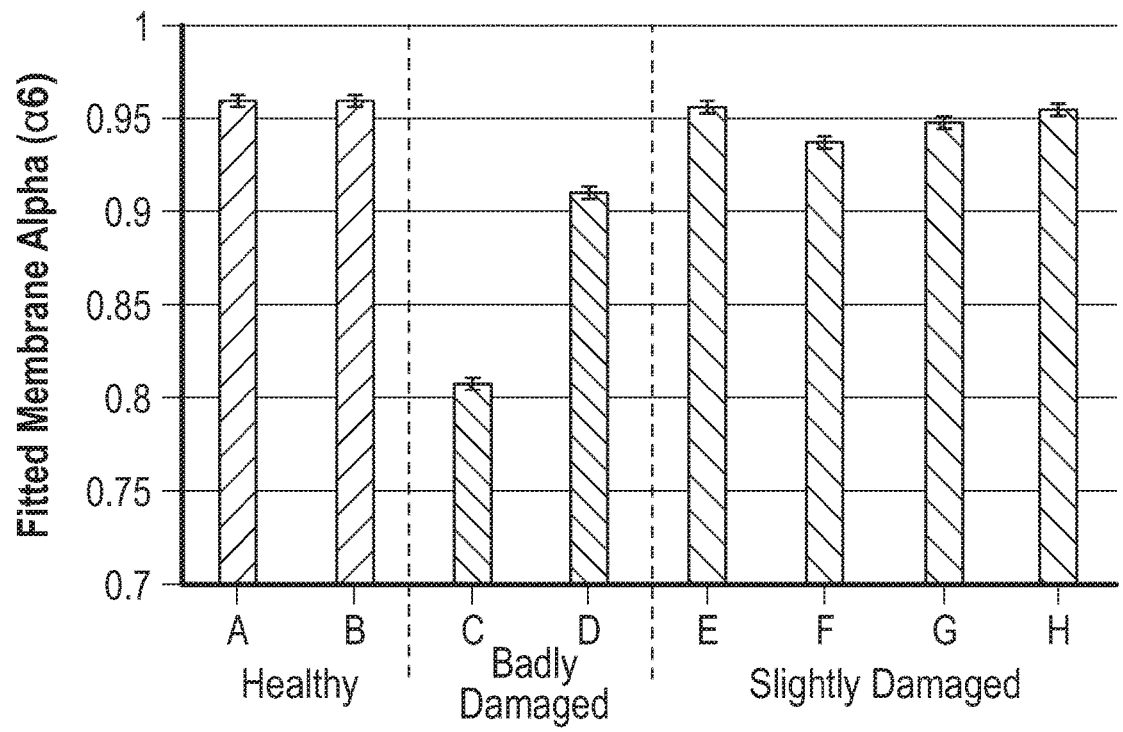
FIG. 11D is a chart that shows fitted membrane alpha for the eight sensors.

FIG. 11D shows fitted membrane alpha for the eight sensors. The healthy sensors (sensors A and B) have fitted membrane alpha values that are higher than the values for the heavily damaged sensors (C and D). The slightly damaged sensors have fitted membrane alpha values that are between values for the healthy sensors and the badly damaged sensors, which indicates that the fitted membrane alpha may be used to distinguish healthy sensors from damaged sensors.

Figure 11E:
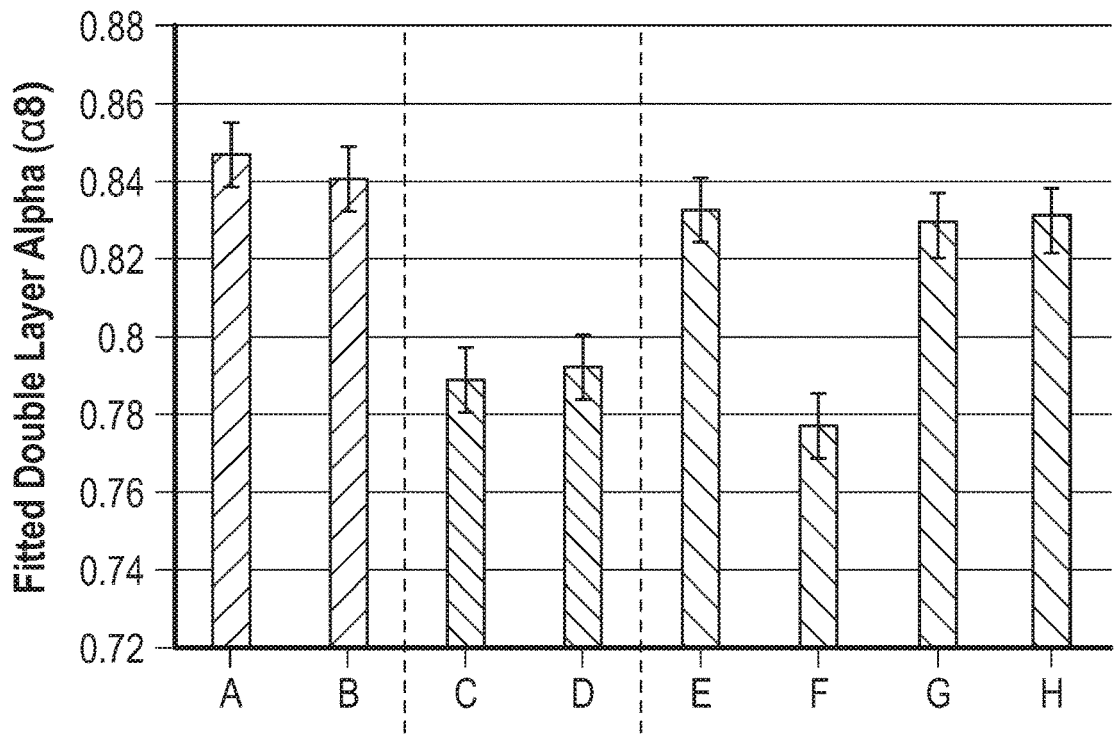
FIG. 11E is a chart that shows fitted double layer alpha for the eight sensors.

FIG. 11E shows fitted double layer alpha for the eight sensors. The healthy sensors (A and B) have fitted double layer alpha values that are significantly higher than the fitted double layer alpha values for the damaged sensors (C and D). The slightly damaged sensors have fitted double layer alpha values that are generally between the values for healthy and highly damaged sensors, with one sensor (sensor F) having a value that is lower than the highly damaged sensors.

In some examples, two or more of the parameters may be used in combination to ascertain whether a sensor is healthy, or damaged, or badly damaged. Using two or more sensors may increase the confidence in the classification of a particular sensor or reduce the likelihood of misclassification. For example, FIG. 11E suggests that sensor F is badly damaged, but the chart in FIG. 11A suggests it is slightly damaged. In some examples, the parameters may be weighted, e.g., the fitted pseudo membrane capacitance or fitted membrane resistance may be weighted more heavily than the other parameters in determining whether a sensor is damaged, or the extent of damage.

Figure 12:
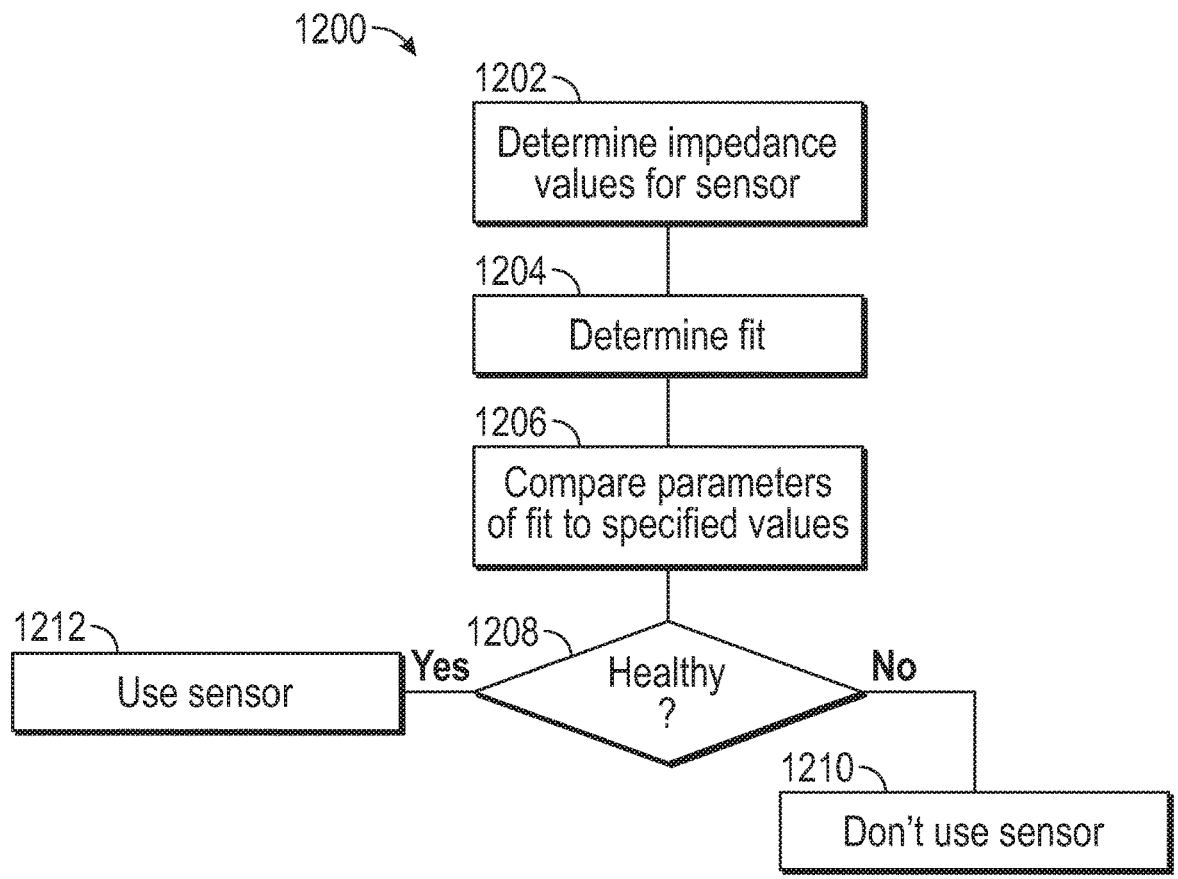
FIG. 12 is a flowchart illustration of a method of assessing a health of a sensor.

FIG. 12 is a flowchart illustration of a method 1200 of assessing a health of a sensor. At operation 1202, an impedance value is determined for a sensor. The impedance value may be determined, for example, by applying a voltage or voltage change, and measuring a current or current change, and using Ohm's law to determine impedance. In some examples, the method may include applying a plurality of signals at different frequencies and determining impedance for the different frequencies.

At operation 1204, a fit may be determined. For example, a fit may be determined for a relationship between impedance and frequency, as described in reference to FIG. 9. At operation 1206, a comparison is made to one or more specified values. For example, a comparison may be made against a reference value or a model or template. In some examples, the comparison may include a fitted parameter such as fitted pseudo membrane capacitance, fitted membrane resistance, fitted pseudo double layer capacitance, fitted membrane alpha, or fitted double layer alpha. In some examples, a comparison may be made for two or more parameters, which may increase a confidence that a sensor has been correctly characterized.

At operation 1208, a health determination may be made about the sensor. For example, the health determination may include a determination about whether the sensor is healthy, or not healthy (e.g., excessively damaged). In some examples, a sensor may be assigned a health status from three or more available classifications (e.g., healthy, slightly damaged, or extensively damaged). In some examples, a quantitative healthy assessment may be made. For example, a degree of damage of a sensor may be determined, based on one or more fit parameters.

At operation 1210, responsive to a determination that a sensor is not healthy, a sensor may be rejected. For example, a sensor may be removed from a manufacturing process (e.g., scrapped), or a user may be notified that the sensor should be replaced. At operation 1212, responsive to a determination that a sensor is healthy, it may be approved for use. In some examples, a sensor that is approved for use may be compensated based on a measured or determined parameter, such as one of the fitted parameters listed above, or based on a determined degree of damage. For example, sensor electronics may apply an adjusted sensitivity or sensitivity curve to compensate for the detected damage or abnormality characteristic in the sensor.

The method 1200 may be performed by sensor electronics (e.g., sensor electronics 106 in FIGS. 1 and 2) that are coupled to a sensor (e.g., sensor 104 in FIG. 1 or sensor 34 in FIGS. 3A-3B) to improve the performance of an analyte sensor system, e.g., to determine a health state of a sensor membrane (e.g., determine an amount of damage or abnormality) and avoid reliance on inaccurate sensor readings from an unhealthy (e.g., excessively damaged) sensor.

Figure 13:
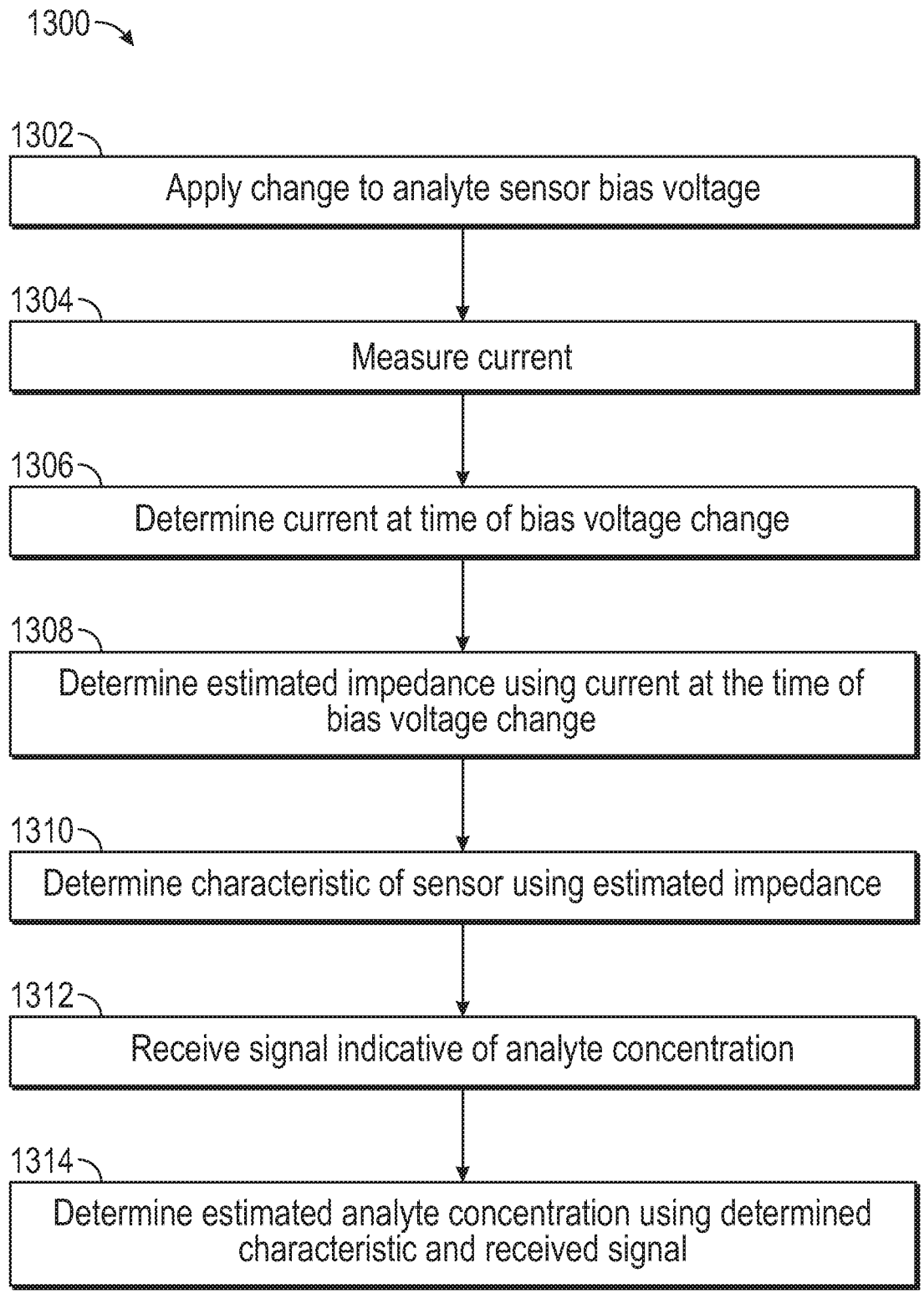
FIG. 13 is a flow chart illustration of a method of operating an analyte sensor system using sensor electronics to correct for an error from double-layer capacitance of a sensor membrane.

FIG. 13 is a flow chart illustration of a method 1300 of operating an analyte sensor system using sensor electronics to correct for an error from double-layer capacitance of a sensor membrane. The method 1300 may be performed by sensor electronics (e.g., sensor electronics 106 in FIGS. 1 and 2) coupled to a sensor (e.g., sensor 104 in FIG. 1 or sensor 34 in FIGS. 3A-3B). The method 1300 may include, at operation 1302, applying a change to an analyte sensor bias voltage, for example as described in reference to FIGS. 5A to 5C.

The method 1300 may include, at operation 1304, measuring a current value for each of a plurality of time periods after application of the bias voltage change. The method 1300 may include, at operation 1306, determining a current at the time of the bias voltage change using the current values for the plurality of time periods. For example, a curve may be extrapolated using current values measured after the bias voltage change to determine a current at the time of the bias voltage change, which may allow for more accurate determination of an impedance, by accounting for a membrane capacitance, as described in reference to FIGS. 8A to 8D. In some examples, the method 1300 may include fitting the current values for the plurality of time periods to an exponential curve and extrapolating the fitted curve to determine the current at the time of the bias voltage change, for example as described in reference to FIGS. 8C and 8D.

The method 1300 may include, at operation 1308, determining an estimated impedance using the determined current at the time of the bias voltage change. The method 1300 may include, at operation 1310, determining a characteristic of the analyte sensor using the estimated impedance. In some examples, determining the characteristic of the analyte sensor may include determining a sensor sensitivity. In some examples, a sensor sensitivity may be updated to account for drift by applying the change to the bias voltage at a second time, measuring the currents for a second plurality of time periods, extrapolating to determine the current at the second time, determining the estimated impedance based on the current at the second time, and determining the characteristic of the sensor at the second time based on the estimated impedance at the second time.

The method 1300 may include, at operation 1312, receiving from the analyte sensor a signal indicative of an analyte concentration. The method 1300 may include, at operation 1314, determining an estimated analyte concentration level using the determined characteristic of the analyte sensor and the received signal.

The method 1300 may be performed by sensor electronics (e.g., sensor electronics 106 in FIGS. 1 and 2) that are coupled to a sensor (e.g., sensor 104 in FIG. 1 or sensor 34 in FIGS. 3A-3B) to improve the performance of an analyte sensor system, e.g., to determine an impedance of or characteristic of a sensor more accurately than conventional methods, which may allow for more accurate determination of estimated analyte concentration methods.

Each of these non-limiting examples in any portion of the above description may stand on its own or may be combined in various permutations or combinations with one or more of the other examples.

The above detailed description includes references to the accompanying drawings, which form a part of the detailed description. The drawings show, by way of illustration, specific embodiments in which the subject matter can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," "third," etc., are used merely as labels, and are not intended to impose numerical requirements on their objects.

Geometric terms, such as "parallel", "perpendicular", "round", or "square" are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the subject matter should be determined with reference to the claims, along with the full scope of equivalents to which such claims are entitled.

What is claimed is:

1. A method of operating an analyte sensor system using sensor electronics, the method comprising:
   applying a bias voltage change to an analyte sensor bias voltage;
   measuring a current response including a current value for each of a plurality of time periods after application of the bias voltage change;
   determining an initial current value at a time of the application of the bias voltage change by at least extrapolating a curve representative of the current value for each of the plurality of time periods, wherein the measured current response does not include the initial current value;
   determining an estimated impedance using the determined initial current value;
   determining a characteristic of an analyte sensor using the estimated impedance;
   receiving from the analyte sensor a signal indicative of an analyte concentration; and
   determining an estimated analyte concentration level using the determined characteristic of the analyte sensor and the received signal.

2. The method of claim 1, wherein measuring the current response value includes integrating a charge over each of the plurality of time periods.

3. The method of claim 1, wherein determining the initial current value includes fitting the curve based at least on using the current values for each of the plurality of time periods.

4. The method of claim 3, wherein fitting the curve includes fitting an exponential curve, wherein the exponential curve accounts for an impact of double-layer capacitance on the current value.

5. The method of claim 1, wherein determining the characteristic of the analyte sensor includes determining a sensitivity of the analyte sensor to the analyte concentration.

6. The method of claim 5, comprising compensating for sensor drift using the estimated impedance or the determined sensitivity.

7. The method of claim 1, wherein determining the characteristic of the analyte sensor includes determining a level of damage or a defect of the analyte sensor.

8. The method of claim 1, wherein determining the characteristic of the analyte sensor includes determining a compensation for the analyte sensor.

9. The method of claim 1, wherein applying the bias voltage change to the analyte sensor bias voltage includes applying a step in the analyte sensor bias voltage.

10. An analyte sensor system comprising:
    an analyte sensor configured to provide a sensor signal indicative of an analyte concentration level; and
    sensor electronics coupled to the analyte sensor, the sensor electronics configured to apply a change to an analyte sensor bias voltage, measure a plurality of current response levels for each of a plurality of respective time periods after application of the change to the analyte sensor bias voltage, derive an initial current response level at a time of the application of the change to the analyte sensor bias voltage by at least extrapolating using the plurality of current response levels for each of the plurality of respective time periods, determine an estimated impedance using the derived initial current response level, receive a signal indicative of an analyte concentration from the analyte sensor, and determine an estimated analyte concentration level based upon the received signal and the estimated impedance, wherein the measured plurality of current response levels does not include the derived initial current response level.

11. The analyte sensor system of claim 10, wherein measuring the plurality of current response levels includes integrating charge over each of the plurality of respective time periods.

12. The analyte sensor system of claim 10, wherein deriving the initial current response level includes fitting a curve using the plurality of measured current response levels.

13. The analyte sensor system of claim 12, wherein fitting the curve includes fitting an exponential curve, wherein the exponential curve accounts for an impact of double-layer capacitance on the plurality of measured current response levels.

14. The analyte sensor system of claim 10, wherein the sensor electronics are configured to determine a sensor sensitivity to the analyte concentration using the estimated impedance, and determine the estimated analyte concentration level using the sensor sensitivity.

15. The analyte sensor system of claim 14, wherein determining the sensor sensitivity includes determining a sensor compensation based on the estimated impedance.

16. The analyte sensor system of claim 10, wherein determining the estimated impedance using the plurality of current response levels accounts for a double-layer membrane capacitance of the analyte sensor.

17. A method of operating an analyte sensor system using sensor electronics to correct for an error from double-layer capacitance of a sensor membrane, the method comprising:
    applying a bias voltage change to an analyte sensor bias voltage;
    measuring a current response comprising a current value for each of a plurality of time periods after application of the bias voltage change;
    determining a current at a time of the bias voltage change by at least extrapolating the measured current response using the current value for each of the plurality of time periods, wherein the current at the time of the bias voltage change is not part of the measured current response;

determining an estimated impedance using the determined current at the time of the bias voltage change;

determining a characteristic of an analyte sensor using the estimated impedance;

receiving from the analyte sensor a signal indicative of an analyte concentration; and determining an estimated analyte concentration level using the determined characteristic of the analyte sensor and the received signal.

18. The method of claim 17, comprising fitting the current value for each of the plurality of time periods to an exponential curve, and extrapolating the curve to determine the current at the time of the bias voltage change.

19. The method of claim 17, wherein determining the characteristic of the analyte sensor includes determining a sensor sensitivity.

20. The method of claim 19, wherein the sensor sensitivity is updated to account for drift by applying a second bias voltage change at a second time, measuring a second current value for each of a second plurality of time periods, extrapolating to determine a second current at the second time, determining the estimated impedance based on the second current at the second time, and determining the characteristic of the analyte sensor at the second time based on the estimated impedance at the second time.

21. An analyte sensor system comprising:
an analyte sensor sized and shaped for insertion into a host and configured to generate a sensor signal indicative of an analyte concentration level; and
sensor electronics coupled to the analyte sensor configured to:
apply a bias voltage change to an analyte sensor bias voltage;
measure a current value for each of a plurality of time periods after application of the bias voltage change;
determine a current at a time of the bias voltage change by at least extrapolating the current value for each of the plurality of time periods, wherein the current at the time of the bias voltage change is not measured by the sensor electronics;
determine an estimated impedance using the determined current at the time of the bias voltage change;
determine a characteristic of the analyte sensor using the estimated impedance;
receive from the analyte sensor a signal indicative of an analyte concentration; and
determine an estimated analyte concentration level using the determined characteristic of the analyte sensor and the received signal.

22. The analyte sensor system of claim 21, wherein the sensor electronics fit the current value for each of the plurality of time periods to an exponential curve and extrapolate the exponential curve to determine the current at the time of the bias voltage change.

23. The analyte sensor system of claim 21, wherein the sensor electronics determine a sensor sensitivity.

24. The analyte sensor system of claim 23, wherein the sensor electronics update the sensor sensitivity to account for drift by applying a second bias voltage change at a second time, measuring a second current value for each of a second plurality of time periods, extrapolating to determine a second current at the second time, determining the estimated impedance based on the second current at the second time, and determining the characteristic of the analyte sensor at the second time based on the estimated impedance at the second time.

25. A method of operating an analyte sensor system using sensor electronics, the method comprising:
applying a bias voltage change to an analyte sensor bias voltage;
measuring a current for one or more time periods after application of the bias voltage change;
determining an estimated impedance based on a non-measured current and a double-layer capacitance value, wherein the non-measured current is derived from the measured current for the one or more time periods after application of the bias voltage;
determining a characteristic of the analyte sensor using the estimated impedance;
receiving from the analyte sensor a signal indicative of an analyte concentration; and
determining an estimated analyte concentration level using the determined characteristic of the analyte sensor and the received signal.

26. The method of claim 25, wherein the double-layer capacitance value is a specified double-layer capacitance estimate for the analyte sensor.

27. The method of claim 25, comprising increasing the analyte sensor bias voltage and measuring a current response to increasing the bias voltage, decreasing the analyte sensor bias voltage and measuring a current response to decreasing the analyte sensor bias voltage, and determining the double-layer capacitance value using the current response to increasing the bias voltage and the current response to decreasing the analyte sensor bias voltage.

28. The method of claim 25, wherein determining the double-layer capacitance value is based on the current for the one or more time periods.

29. An analyte sensor system comprising:
an analyte sensor sized and shaped for insertion into a host and configured to generate a sensor signal indicative of an analyte concentration level; and
sensor electronics coupled to the analyte sensor, the sensor electronics configured to:
apply a change to an analyte sensor bias voltage;
measure a current for one or more time periods after application of the change to the analyte sensor bias voltage;
determine an estimated impedance based on a non-measured current and a double-layer capacitance value, wherein the non-measured current is derived from the measured current for the one or more time periods after application of the bias voltage;
determine a characteristic of the analyte sensor using the estimated impedance;
receive from the analyte sensor a signal indicative of an analyte concentration; and
determine an estimated analyte concentration level using the determined characteristic of the analyte sensor and the received signal.

30. The analyte sensor system of claim 29, wherein the double-layer capacitance value is a specified double-layer capacitance estimate for the analyte sensor.

31. The analyte sensor system of claim 29, wherein the sensor electronics are configured to increase the analyte sensor bias voltage and measure a current response to increasing the analyte sensor bias voltage, decrease the analyte sensor bias voltage and measure a current response to decreasing the analyte sensor bias voltage, and determine the double-layer capacitance value using the current response to increasing the bias voltage and the current response to decreasing the bias voltage.

32. The analyte sensor system of claim 29, wherein the sensor electronics are configured to determine the double-layer capacitance value based on the currents for a plurality of time periods.

* * * * *